(12) United States Patent
Moll Neto et al.

(10) Patent No.: US 10,688,275 B2
(45) Date of Patent: Jun. 23, 2020

(54) DEVICES, SYSTEMS AND METHODS FOR DELIVERING COFFEE-DERIVED VOLATILES

(71) Applicant: Jorge Neval Moll Neto, Palo Alto, CA (US)

(72) Inventors: Jorge Neval Moll Neto, Palo Alto, CA (US); Silvia Siag Oigman, Rio de Janeiro (BR); Jeffrey J. Christian, Morgan Hill, CA (US); Benjamin Scott Arnett, Hollister, CA (US)

(73) Assignee: Jorge Neval Moll Neto, Palo Alto, CA (US)

( * ) Notice: Subject to any disclaimer, the term of this patent is extended or adjusted under 35 U.S.C. 154(b) by 294 days.

(21) Appl. No.: 15/724,007

(22) Filed: Oct. 3, 2017

(65) Prior Publication Data

US 2018/0093067 A1 Apr. 5, 2018

Related U.S. Application Data

(60) Provisional application No. 62/403,607, filed on Oct. 3, 2016.

(51) Int. Cl.
*A61M 21/02* (2006.01)
*A61K 36/74* (2006.01)
(Continued)

(52) U.S. Cl.
CPC ........... *A61M 21/02* (2013.01); *A61K 9/0073* (2013.01); *A61K 36/74* (2013.01);
(Continued)

(58) Field of Classification Search
CPC ..... A24F 47/002; A61K 9/0043; A61K 36/74; A61K 9/0073; A61M 2205/3569;
(Continued)

(56) References Cited

U.S. PATENT DOCUMENTS 4,083,372 A 4/1978 Boden
4,149,548 A 4/1979 Bradshaw
(Continued)

OTHER PUBLICATIONS

Aromatherapy for people in recovery.Sep. 2016. Available at: http://alcoholrehab.com/drug-addiction-treatment/aromatherapy-for-people-in-recovery. Accessed on: Nov. 1, 2017. (Year: 2016).*
(Continued)

*Primary Examiner* — Christine H Matthews
*Assistant Examiner* — Joshua Daryl D Lannu
(74) *Attorney, Agent, or Firm* — Wilson Sonsini Goodrich and Rosati, P.C.

(57) ABSTRACT

Devices, systems and methods are provided for delivering coffee-derived volatiles to a user, particularly for the treatment of addiction. The coffee volatiles are selected and delivered by devices and systems which allow for concentrated delivery to the olfactory system of the user in a controlled manner. The olfactory system is the part of the sensory system used for smelling or olfaction. Olfaction of such coffee volatiles in this prescribed fashion stimulates the reward system of the brain such that a specific desired outcome is achieved. In some embodiments, the desired outcome is a reduction in addiction symptoms or curbing of a sensation of addiction withdrawal.

46 Claims, 18 Drawing Sheets

(51) Int. Cl.
| | |
|---|---|
| A61K 9/00 | (2006.01) |
| A61M 15/00 | (2006.01) |
| A61M 15/06 | (2006.01) |
| A61M 15/08 | (2006.01) |
| A61M 11/00 | (2006.01) |
| A61M 11/04 | (2006.01) |
| A24F 47/00 | (2020.01) |
| A61M 21/00 | (2006.01) |

(52) U.S. Cl.
CPC ...... *A61M 15/0001* (2014.02); *A61M 15/003* (2014.02); *A61M 15/06* (2013.01); *A61M 15/08* (2013.01); *A24F 47/002* (2013.01); *A61K 9/0043* (2013.01); *A61M 11/005* (2013.01); *A61M 11/007* (2014.02); *A61M 11/042* (2014.02); *A61M 15/001* (2014.02); *A61M 15/009* (2013.01); *A61M 2021/0016* (2013.01); *A61M 2021/0077* (2013.01); *A61M 2205/18* (2013.01); *A61M 2205/3569* (2013.01); *A61M 2205/75* (2013.01); *A61M 2205/8206* (2013.01)

(58) Field of Classification Search
CPC ........ A61M 2205/8206; A61M 11/007; A61M 11/042; A61M 15/001; A61M 15/0001; A61M 2205/18; A61M 2021/0077; A61M 2021/0016; A61M 21/02; A61M 2205/75; A61M 15/06; A61M 15/009; A61M 15/003; A61M 15/08; A61M 11/005
See application file for complete search history.

(56) References Cited

U.S. PATENT DOCUMENTS

| | | | |
|---|---|---|---|
| 4,765,347 | A | 8/1988 | Sensabaugh, Jr. et al. |
| 4,913,168 | A | 4/1990 | Potter et al. |
| 7,820,210 | B2 | 10/2010 | Vail et al. |
| 8,881,737 | B2 | 11/2014 | Collett et al. |
| 8,991,402 | B2 | 3/2015 | Bowen et al. |
| 9,408,416 | B2 | 8/2016 | Monsees et al. |
| 9,687,027 | B2 | 6/2017 | Poston et al. |
| 2005/0169849 | A1* | 8/2005 | Farr ............ A24F 47/002 424/46 |
| 2005/0241658 | A1* | 11/2005 | Pera ............ A23G 3/36 131/352 |
| 2008/0187609 | A1* | 8/2008 | Vail ............ A61K 36/53 424/747 |
| 2010/0284783 | A1* | 11/2010 | Lolmede ......... A61L 9/122 415/1 |
| 2014/0209096 | A1* | 7/2014 | Cheyene ......... A61M 15/08 128/203.12 |
| 2016/0001035 | A1 | 1/2016 | Keener |
| 2017/0064995 | A1 | 3/2017 | Beeson |

OTHER PUBLICATIONS

Amaral, Characterisation and application of ionic liquid capillary columns to the analysis of coffee volatile compounds by gas chromatography mass spectrometry. Analytical & Bioanalytical Chemistry. 2017. 43 Pages.

Araujo, et al., Validation of the Brazilian version of Questionnaire of Smoking Urges-Brief. Rev Psiquiatr Clin. 2007; 34: 166-175.

Aromatherapy for people in recovery. 2016. Available at: http://alcoholrehab.com/drug-addiction-treatment/aromatherapy-for-people-in-recovery. Accessed on: Nov. 1, 2017.

Baker, et al., The Effects of the Nicotine Patch vs. Varenicline vs. Combination Nicotine Replacement Therapy on Smoking Cessation at 26 Weeks: A Randomized Controlled Trial. JAMA. Jan. 26, 2016; 315(4): 371-379.

Cocaine: How is cocaine addiction treated? NIDA. May 2016. Available at: https://www.drugabuse.gov/publications/research-reports/cocaine/what-treatments-are-effective-cocaine-abusers. Accessed on: Feb. 17, 2018.

Cocaine: What are the short-term effects of cocaine use? National Institute on Drug Abuse (NIDA). May 2016. Available at: https://www.drugabuse.gov/publications/research-reports/cocaine/what-are-short-term-effects-cocaine-use. Accessed on: Feb. 17, 2018.

Collins, N., Why does coffee never taste as good as it smells? The Telegraph. Sep. 2012. Available at: http://www.telegraph.co.uk/news/science/9528936/Why-does-coffee-never-taste-as-good-as-it-smells.html. Accessed on: Feb. 17, 2018.

Drugs, Brains, and Behavior: The Science of Addiction. NIH. 2014. Available at: https://www.drugabuse.gov/publications/drugs-brains-behavior-science-addiction/addiction-health. Accessed on: Feb. 17, 2018.

Global information system on alcohol and health (GISAH). World Health Organization. 2018. Available at: http://www.who.int/gho/alcohol/en/. Accessed on: Feb. 17, 2018.

PCT/US2017/054955 International Search Report dated Dec. 5, 2017.

Public health dimension of the world drug problem. World Health Organization. Mar. 27, 2017. Available at:http://apps.who.int/gb/ebwha/pdf_files/WHA70/A70_29-en.pdf. Accessed on: Feb. 17, 2018.

Tobacco. World Health Organization. May 2017. Available at: http://www.who.int/mediacentre/factsheets/fs339/en/. Accessed on: Feb. 17, 2018.

Van Den Dool, et al., A generalization of the retention index system including linear temperature programmed gas-liquid partition chromatography. J Chromatography, 1963; 11:463-471.

Volkow, et al., Opioid Abuse in Chronic Pain—Misconceptions and Mitigation Strategies. The new England journal of medicine. 2016; 374:1253-1263.

What are treatments for tobacco dependence? Tobacco, Nicotine, and E-Cigarettes. NIH. Jan. 2018. Available at: https://www.drugabuse.gov/publications/research-reports/tobacco/are-there-effective-treatments-tobacco-addiction. Accessed on: Feb. 17, 2018.

Wu, Li-Tzy, Substance abuse and rehabilitation: responding to the global burden of diseases attributable to substance abuse. Substance Abuse and Rehabilitation. 2010; 1:5-11.

* cited by examiner

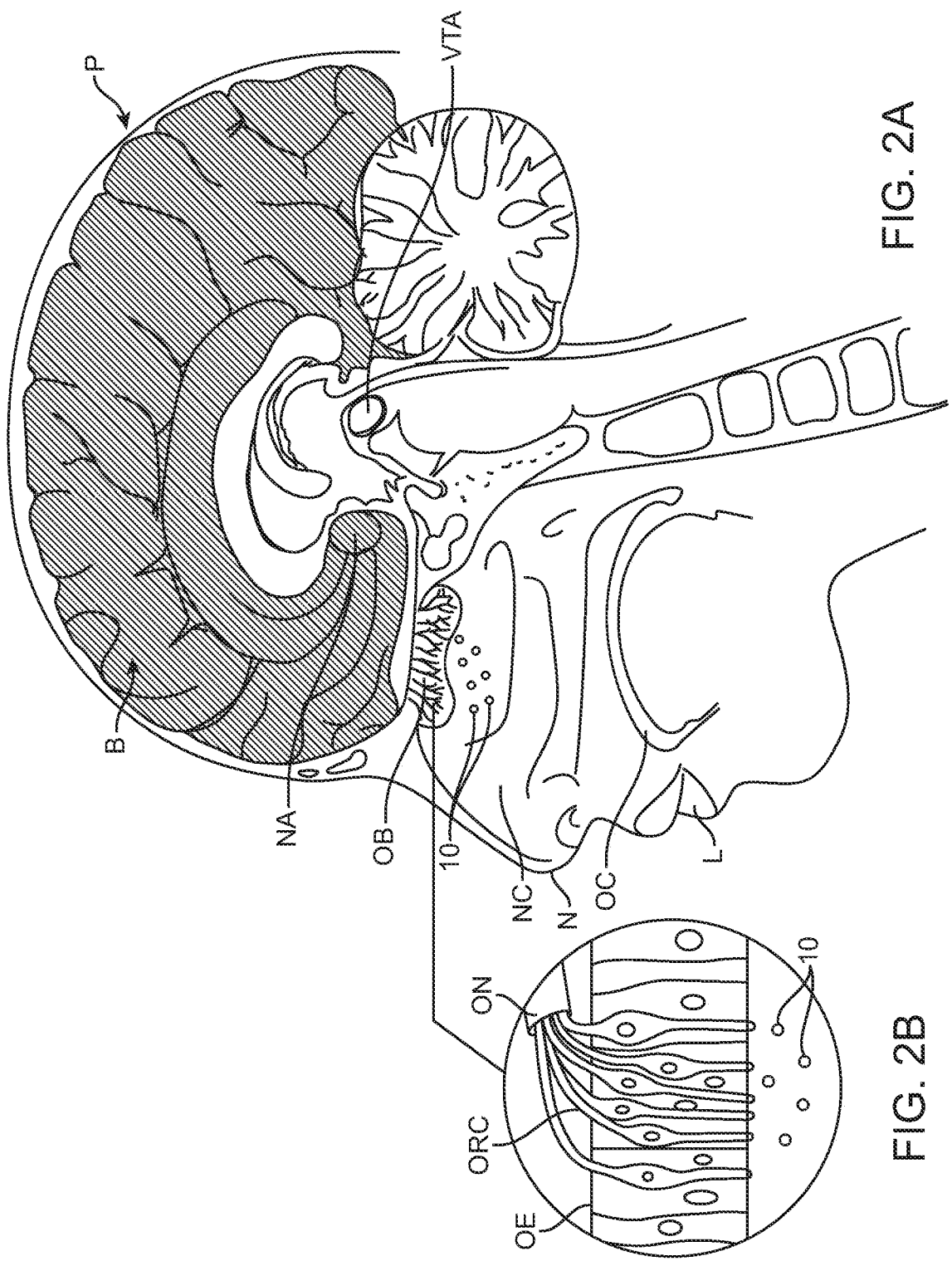

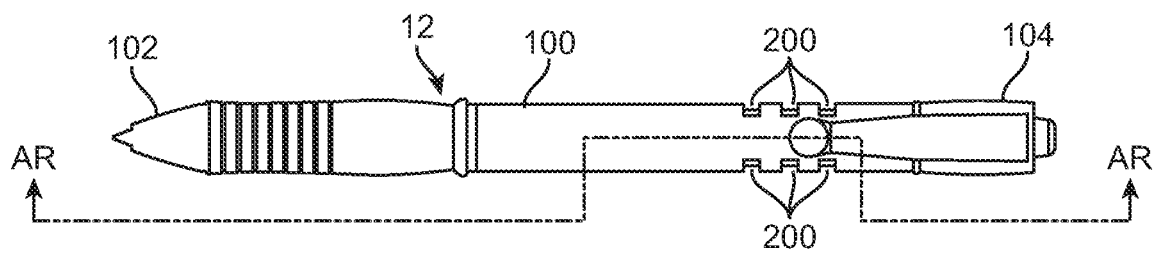
FIG. 20
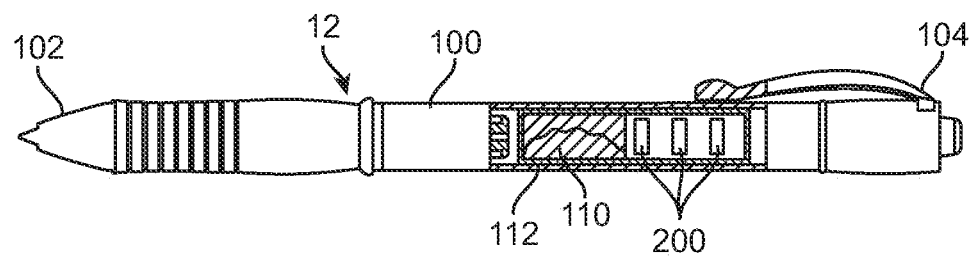
FIG. 21
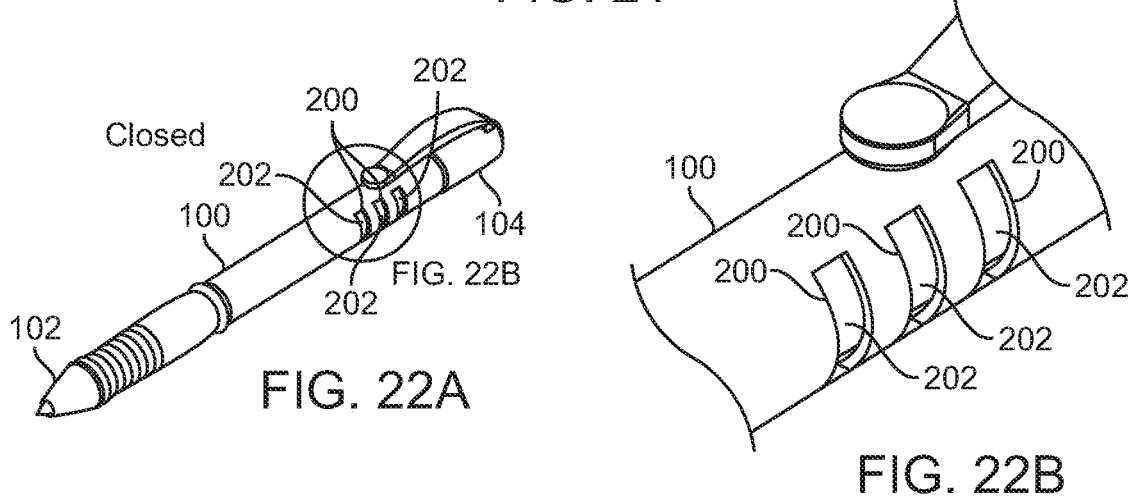
FIG. 22A
FIG. 22B
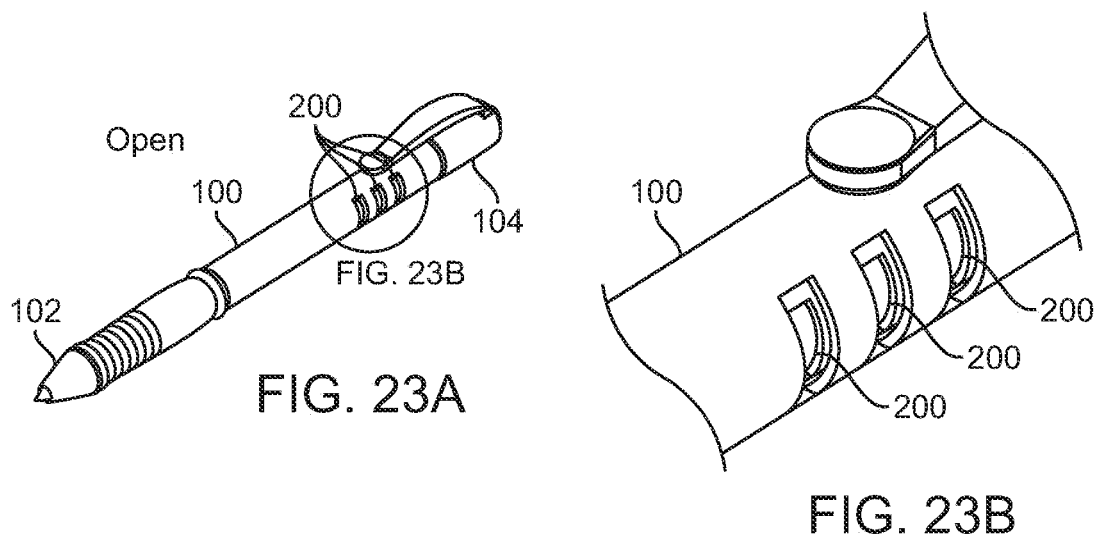
FIG. 23A
FIG. 23B

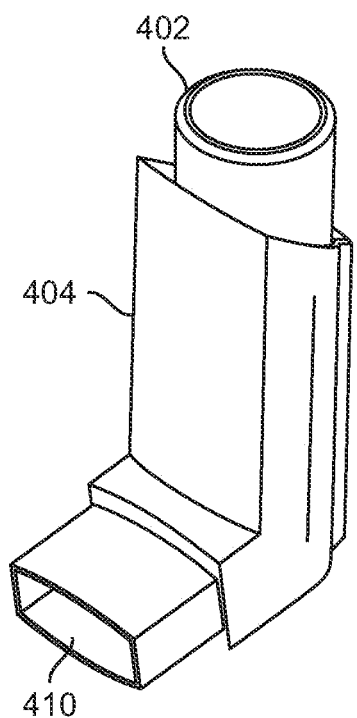 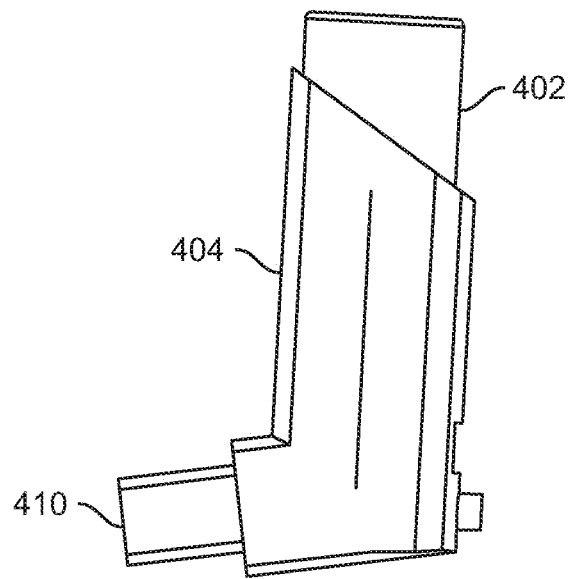
FIG. 25A  FIG. 25B
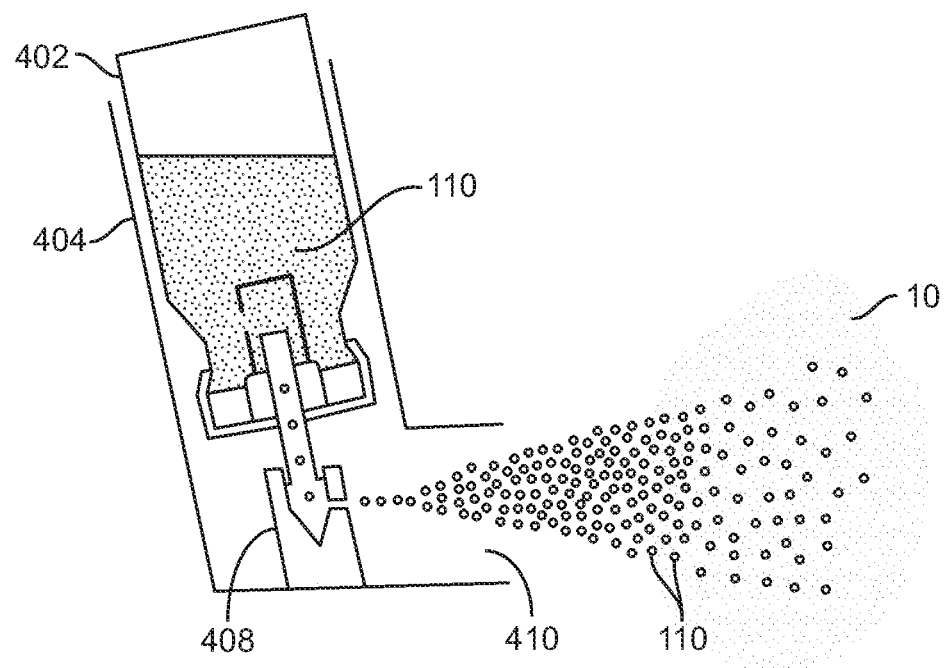
FIG. 26

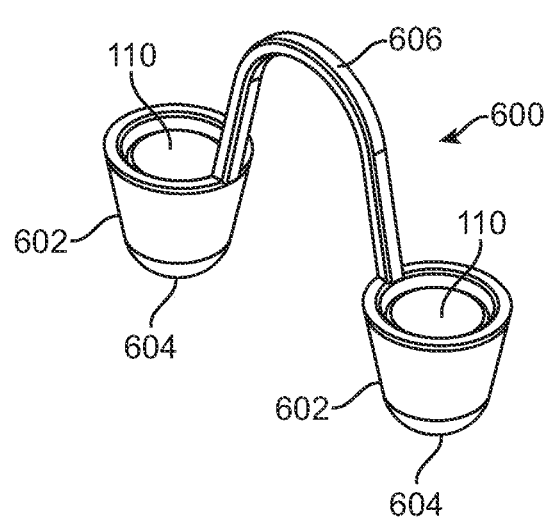
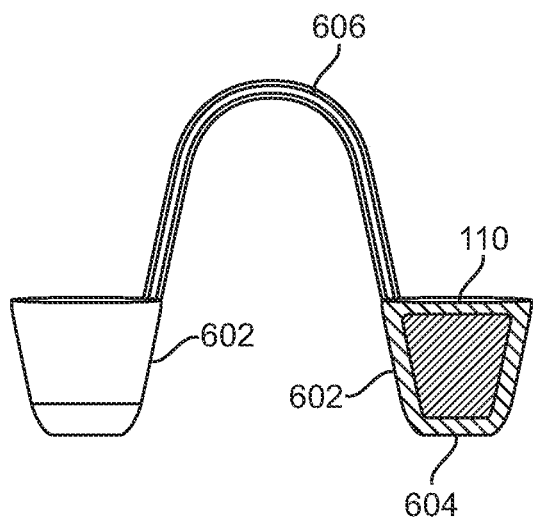
FIG. 29A  FIG. 29B
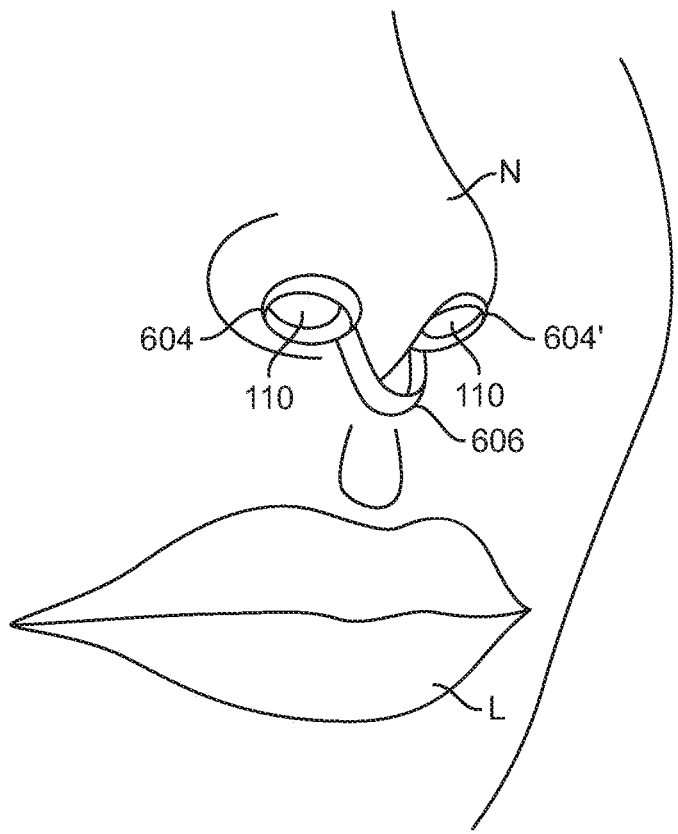
FIG. 29C

DEVICES, SYSTEMS AND METHODS FOR DELIVERING COFFEE-DERIVED VOLATILES

CROSS-REFERENCE TO RELATED APPLICATIONS

This application claims the benefit of priority to Provisional No. 62/403,607, filed Oct. 3, 2016, entitled METHOD AND APPARATUS FOR RETRONASAL/ORTHONASAL DELIVERY OF COFFEE AND ITS VOLATILES, the entire content of which is incorporated herein by reference.

BACKGROUND OF THE INVENTION

Drug abuse is a major public health concern that impacts society on multiple levels. Alcohol, tobacco, and illegal drug use are pervasive throughout the world. Substance abuse problems are among the major contributors to the global disease burden, which includes disability and mortality. The main health consequences of drug misuse are the development of cardiovascular diseases, cancer, an increased likelihood of contracting HIV, hepatitis, and other infectious diseases and neurological effects. The harmful use of alcohol results in the death of 3.3 million people annually, while tobacco kills up to half of its users, which is more than 7 million people each year (including both smokers and non-smokers, via second-hand smoking).

Drugs of abuse (including alcohol) are inherently rewarding. As an example, cocaine can lead to a euphoric state, energetic feelings, talkative dispositions and mental alertness. Cocaine helps them perform simple physical and intellectual tasks more quickly. Heroin produces a sense of well-being and euphoria. Nicotine improves concentration, attention and memory, and reduces reaction times. These effects are the motivation to be consumed by humans or self-administered by laboratory animals.

Repeated use of such drugs usually leads to tolerance and dependence, conditions in which progressively higher doses are required to maintain initial drug effectiveness and in which abrupt drug abstinence results in a large withdrawal syndrome. In the case of heroin, withdrawal involves thermoregulatory problems (chills and sweats), gastrointestinal (cramps, diarrhea) disturbances and significant painful dysphoria. When the drug is cocaine, the effects include dysphoria (mild depression), fatigue, sleep disturbances, increased appetite and anxiety. Nicotine withdrawal includes dysphoria, insomnia, anxiety, restlessness, decreased heart rate and weight gain.

Drug addiction is a complex disease involving changes in the brain as well as a wide range of social, familial, and other environmental factors. The benefits of treatment far outweigh the economic costs. Despite the availability of treatment services, however, the vast majority of people with substance use disorders do not seek or use treatment. Problems require combined research and policy-making efforts from all parts of the world to establish a viable knowledge base to inform for prevention, risk-reduction intervention, effective use of evidence-based treatment, and rehabilitation for long-term recovery.

Presently, there are no medications approved by the U.S. Food and Drug Administration to treat cocaine addiction, though researchers are exploring a variety of neurobiological targets.

The use of opioid-agonist medications such as methadone and buprenorphine for opioid addiction has led to the misconception that such drugs are just substitutes for the opioid being abused. Although these medications are opioid agonists, their slower brain pharmacokinetics along with their more stable concentrations help to stabilize physiologic processes that are disrupted by intermittent abuse of opioids. The use of these drugs also protects against risks associated with opioid abuse while facilitating recovery. However, treatment for opioid dependence is not always available due to a limited number of providers, waiting lists to access treatment, or laws that prevent their use.

The first pharmacological treatments approved by the U.S. Food and Drug Administration for smoking cessation were nicotine replacement therapies (NRTs), such as nicotine gum and a transdermal nicotine patch. One benefit of these therapies is that these forms of nicotine have little abuse potential since they do not produce the pleasurable effects of tobacco products, nor do they contain the carcinogens and gases associated with tobacco smoke. When NRTs are used in conjunction with behavioral support, the treatment successful is bigger. However, whereas nicotine gum provides some smokers with the desired control over dose and the ability to relieve cravings, others are unable to tolerate the taste and chewing demands. Skin reactions are one of the more common side-effects of nicotine patches. Other treatments are also available, such as Varenicline tartrate (Chantix), which is a medication that also received FDA approval for smoking cessation. Varenicline and combination nicotine replacement therapy (C-NRT) are the most efficient conventional therapies, but Varenicline produces significant adverse events like vivid dreams, insomnia, nausea, constipation, sleepiness, and indigestion. In any case, quitting smoking has been found to be very difficult. Within 6 months, 75-80 percent of people who try to quit smoking relapse.

The neurobiology underlying drug abuse has led to the recognition of addiction as a chronic disease of the brain. Therefore, additional treatment options are needed to combat this disease without the drawbacks and disadvantages associated with current methods. Such treatment options should be readily available, easy to use, cost effective, safe and effective. At least some of these objectives will be met by the present invention.

SUMMARY OF THE INVENTION

The present invention generally relates to systems, devices and methods for delivering volatiles to a user, and more particularly relates to delivering coffee-derived volatiles to a user, such as for medical purposes or treatments.

In a first aspect of the present invention, a device is provided for delivering coffee-derived volatiles to a user comprising a housing body, a quantity of coffee substance disposed within the housing body, wherein coffee-derived volatiles are collectable from the coffee substance within the housing body without the use of heat, and an actuatable mechanism for allowing delivery of the coffee-derived volatiles from the housing body in a form of a dose, wherein the dose is sufficient to cause olfactory stimulation of a ventral tegmental area or nucleus accumbens of a brain reward system of the user in an intensity equivalent to an addictive drug.

Typically, the addictive drug to which the intensity is equivalent is heroin, cocaine, alcohol, opioids, nicotine, amphetamine, methamphetamine, caffeine or their synthetic analogs. In some embodiments, the intensity is sufficient to curb a withdrawal sensation of an addiction.

In some embodiments, the coffee substance comprises ground coffee and the quantity of ground coffee is 10 grams.

It may be appreciated that in some embodiments the coffee substance comprises whole coffee beans, ground coffee, coffee oil, single or mixed coffee molecules, or any combination of these.

In some embodiments, the quantity of coffee substance is provided in a removable cartridge. Optionally, the cartridge may have at least one puncturable wall, and the actuation mechanism may comprise a protrusion configured to puncture the puncturable wall upon actuation so as to allow the delivery of the coffee-derived volatiles.

In some embodiments, the cartridge is sufficiently flexible to allow the user to reversibly deform the cartridge so as to further process the coffee substance therein. It may be appreciated that the removable cartridge is optionally pre-filled and sealed, or optionally refillable by the user. In some embodiments, the quantity of coffee substance is provided in a plurality of removable cartridges, wherein the plurality of removable cartridges is positionable within the housing body.

In some embodiments, the actuatable mechanism comprises an internal airflow accelerator configured to propel the volatiles. In some embodiments, the actuatable mechanism comprises a depressible button, wherein depression of the button actuates the actuatable mechanism.

In some embodiments, the device further comprises at least one outlet opening disposed along the housing body and configured for passage of the coffee-derived volatiles from the housing body. In such embodiments, the actuatable mechanism may comprise at least one cover that is moveable from a first position which blocks the at least one outlet opening from passage of the coffee-derived volatiles to a second position which exposes the at least one outlet opening for passage of the coffee-derive volatiles. Or, in some embodiments, the at least one outlet opening comprises a plurality of outlet openings arranged to provide simultaneous orthonasal and retronasal delivery of the coffee-derived volatiles.

In some embodiments, the housing body has a form of an elongate shaft. In such embodiments, the actuatable mechanism may comprise an end cap joinable with an end of the elongate shaft, wherein joining of the end cap with the end of the elongate shaft actuates the actuation mechanism. Further, the quantity of coffee substance may be provided in a removable cartridge having at least one puncturable wall, wherein the end cap includes a protrusion configured to puncture the puncturable wall upon joining of the end cap with the end of the elongate shaft. In some embodiments, the elongate shaft resembles a cigarette, e-cigarette or cigar. In other embodiments, the elongate shaft resembles a pen or writing implement. In some embodiments, the elongate shaft is insertable into a receptacle on a keychain, watch, hat, article of clothing, mobile phone case, mobile phone, smart phone, Dictaphone, tablet, computer, music player, headphone, glasses case, sunglass case, water bottle, or clip. In some embodiments, the housing body has the form of a nose plug or nostril cover.

It may be appreciated that in some embodiments, the device further comprises a filter configured to inhibit delivery of the coffee substance from the housing body. In addition, it may be appreciated that in some embodiments the device further comprises an alert mechanism configured to deliver an alert at a plurality of predetermined time periods, wherein the time periods correspond to a pattern of an addiction.

In a second aspect of the present invention, a method is provided for treating an addiction of a patient comprising providing a delivery device configured to deliver coffee-derived volatiles upon actuation, wherein the coffee-derived volatiles are generated by the delivery device without the use of heat and the delivery device includes at least one outlet opening for passage of the volatiles therethrough, positioning the delivery device in relation to the patient so that the at least one outlet opening is within a distance which allows olfactory stimulation of the patient by the coffee-derived volatiles upon its delivery, and actuating the delivery device upon a sensation of addiction withdrawal, wherein actuating delivers a dose of coffee-derived volatiles through the at least one outlet opening to the patient which causes olfactory stimulation a brain reward system of the patient in an intensity sufficient to curb the sensation of addiction withdrawal.

In some embodiments, the addiction comprises nicotine addiction, opioid addiction, cocaine addiction, methamphetamine addiction, heroin addiction or alcohol addiction. In some embodiments, the sensation of addiction withdrawal comprises irritability, restlessness, anxiety, depression, sleeplessness or cravings.

In some embodiments, the olfactory stimulation comprises orthonasal stimulation and positioning the delivery device comprises holding the at least one outlet opening within 3 cm of a nostril of the patient. In other embodiments, the olfactory stimulation comprises retronasal stimulation and positioning the delivery device comprises positioning the at least one outlet opening within an oral cavity of the patient.

In some embodiments, providing a delivery device comprises inserting a coffee substance into the delivery device. In some embodiments, inserting a coffee substance comprises inserting a pre-filled cartridge containing the coffee substance into the delivery device. Thus, in some embodiments, actuating the delivery device comprises puncturing the cartridge so as to allow escape of coffee-derived volatiles. In some embodiments, the method further comprises reversibly deforming the cartridge so as to further process the coffee substance therein.

In some embodiments, actuating the delivery device comprises opening a cover over at least one of the at least one outlet openings. In some instances, actuating the delivery device is undertaken in accordance with a predetermined schedule.

In some embodiments, the method further comprises programming the delivery device to provide an alert at a predetermined time indicating a preferred time to actuate the delivery device. In some embodiments, programming the delivery device comprises programming the delivery device to provide a series of alerts at predetermined times indicating a series of preferred times to actuate the delivery device according to a schedule related to treatment of the addiction.

In some embodiments, the method further comprises attaching the delivery device to a keychain, watch, hat, article of clothing, mobile phone case, mobile phone, smart phone, Dictaphone, tablet, computer, music player, headphone, glasses case, sunglass case, water bottle, or clip.

In a third aspect of the present invention, a system is provided for treating an addiction of a patient comprising a plurality of delivery devices, wherein each delivery device has a quantity of coffee substance therein from which coffee-derived volatiles are collectable and deliverable in the form of a dose, and a dosage schedule which prescribes a time sequence for administering each dose to the patient so as to treat the addiction.

In some embodiments, at least some of the quantity of coffee substance within each of the plurality of delivery devices differs so as to provide differing doses. In some embodiments, the differing doses incrementally decrease and the dosage schedule prescribes decreasing doses throughout the time sequence.

In some embodiments, the addiction is a nicotine addiction and each of the plurality of delivery devices resembles a cigarette, e-cigarette or cigar.

In some embodiments, the dose is sufficient to cause olfactory stimulation of a ventral tegmental area or nucleus accumbens of a brain reward system of the patient in an intensity equivalent to an addictive drug.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A illustrates a user having coffee-derived volatiles delivered to the nasal cavity and olfactory bulb.

FIG. 2B is a close-up illustration of a portion of the olfactory bulb of FIG. 2A.

FIG. 20 is a top view illustration of the delivery device of FIG. 19.

FIG. 21 is a side view with a partial cross section of the delivery device of FIG. 20.

FIG. 22A illustrates the delivery device of FIGS. 20-21 in the "closed" position wherein the one or more covers obstruct the vent holes 200.

FIG. 22B is a close-up view of the vent holes and covers of FIG. 22A.

FIG. 23A illustrates the device of FIGS. 20-21 in the "open" position wherein the one or more covers are removed from obstructing the vent holes.

FIG. 23B is a close-up view of the open vent holes of FIG. 23A.

FIGS. 25A-25B, FIG. 26 illustrate an embodiment of a volatile dispensing inhaler.

FIGS. 29A-29C illustrate an embodiment of a coffee-derived volatile dispensing nose plug.

DETAILED DESCRIPTION OF THE INVENTION

Figure 1A:
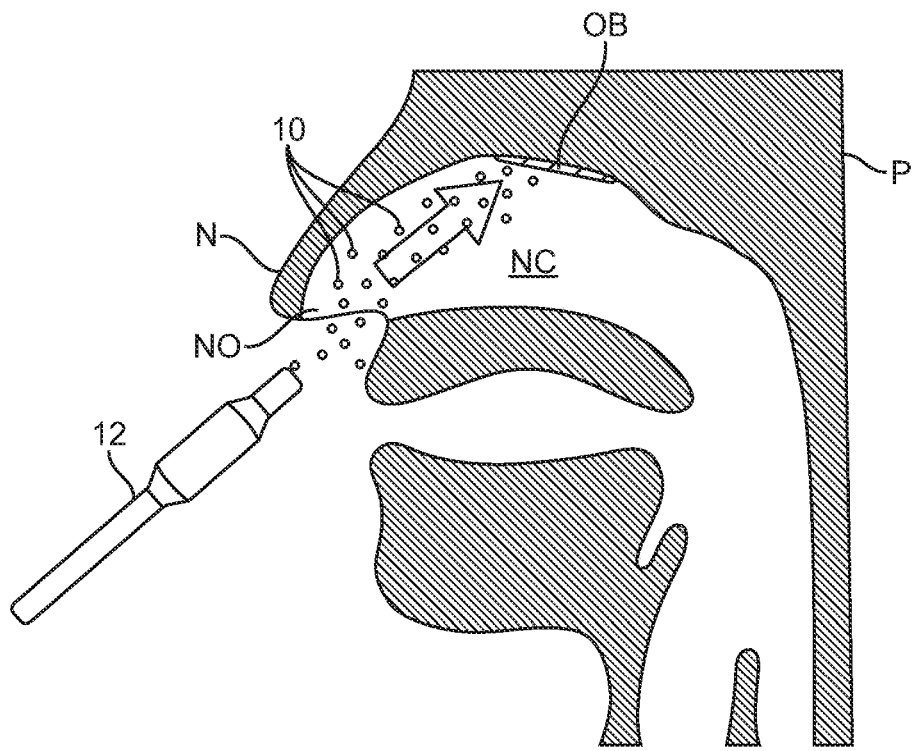
FIG. 1A illustrates an orthonasal delivery route to deliver coffee-derived volatiles via the nose.

Specific embodiments of the disclosed devices, systems, and methods will now be described with reference to the drawings. Nothing in this detailed description is intended to imply that any particular component, feature, or step is essential to the invention.

Devices, systems and methods are provided for delivering coffee-derived volatiles to a user, particularly for the treatment of addiction. The coffee volatiles are selected and delivered by devices and systems which allow for concentrated delivery to the olfactory system of the user in a controlled manner. The olfactory system is the part of the sensory system used for smelling or olfaction. Olfaction of such coffee volatiles in this prescribed fashion stimulates the reward system of the brain such that a specific desired outcome is achieved. In some embodiments, the desired outcome is a reduction in addiction symptoms or curbing of a sensation of addiction withdrawal. This is possible, at least in part, due to the unexpected potency of coffee volatiles in stimulating the reward system when delivered in this manner; such potency is comparable to stimulant drugs such as cocaine, opioids and nicotine. Such outcomes are not achievable with uncontrolled inhalation of coffee volatiles, such as in coffee shops or when drinking coffee, even though such inhalation is typically considered to be generally pleasurable. In addition, inhalation of coffee-scented air fresheners or aromatherapy diffusers are not only uncontrolled but likely they are poor in coffee volatiles.

The smell of freshly brewed coffee is widely appreciated. For millions, likely billions, of people around the world, the scent of freshly brewed coffee represents a trigger for a start of well-motivated day. The beverage is consumed daily around the world (two billion cups of coffee each day) making coffee the third most consumed beverage, second only to water and tea. Even among those who don't drink coffee, many enjoy its aroma. Coffee consumption is mainly attributed to its aroma and flavor, which promote a nearly universal feeling of pleasure and satisfaction. However, with coffee consumption comes a variety of risks and drawbacks. Coffee has a high caffeine content, typically 135 milligrams per 8 ounces of coffee. Consuming more than 500-600 mg of caffeine a day may lead to insomnia, nervousness, restlessness, irritability, a fast heartbeat and even muscle tremors. One study suggests that consuming 300 mg of caffeine a day during pregnancy may increase the risk of low birth weight babies, while other research suggests that drinking four cups of coffee a day may increase the risk of early death. Caffeine is also a diuretic and can increase dehydration. Elevated urinary excretion minerals such as calcium, magnesium and potassium have been noted in coffee drinkers. An imbalance in the electrolyte status can lead to serious systemic complications. It also interferes with iron absorption. In addition, the acidity of coffee is associated with digestive discomfort, indigestion, heartburn, GERD and dysbiosis (imbalances in gut flora). Constituents in coffee can also interfere with normal drug metabolism and detoxification in the liver making it difficult to regulate the normal detoxification process in the liver. Therefore, although coffee consumption is considered pleasurable by many, the side effects and health risks are significant enough to cause many users to reduce consumption or avoid consumption altogether.

The devices, systems and methods of the present invention isolate olfaction of coffee-derived volatiles from coffee consumption, therefore allowing olfaction without the drawbacks of coffee consumption. In addition, volatiles 10 and associated aroma profiles provided herein are not the same as those derived from drinking a cup of coffee. Delivering coffee-derived volatiles 10 according to the methods and devices described herein does not involve drinking and is not associated with taste. The methods and devices rely on olfactory stimulation alone, particularly via orthonasal and retronasal pathways, which does not include taste, oral sensation, or other similar stimulation. In addition, the methods and devices described herein involve controlled phasic delivery which is not achieved when drinking coffee or when exposed to environmental coffee-derived volatiles. The devices, systems and methods provide olfaction of coffee-derived volatiles in a controlled manner so as to effectively stimulate the brain's reward system.

Figure 1B:
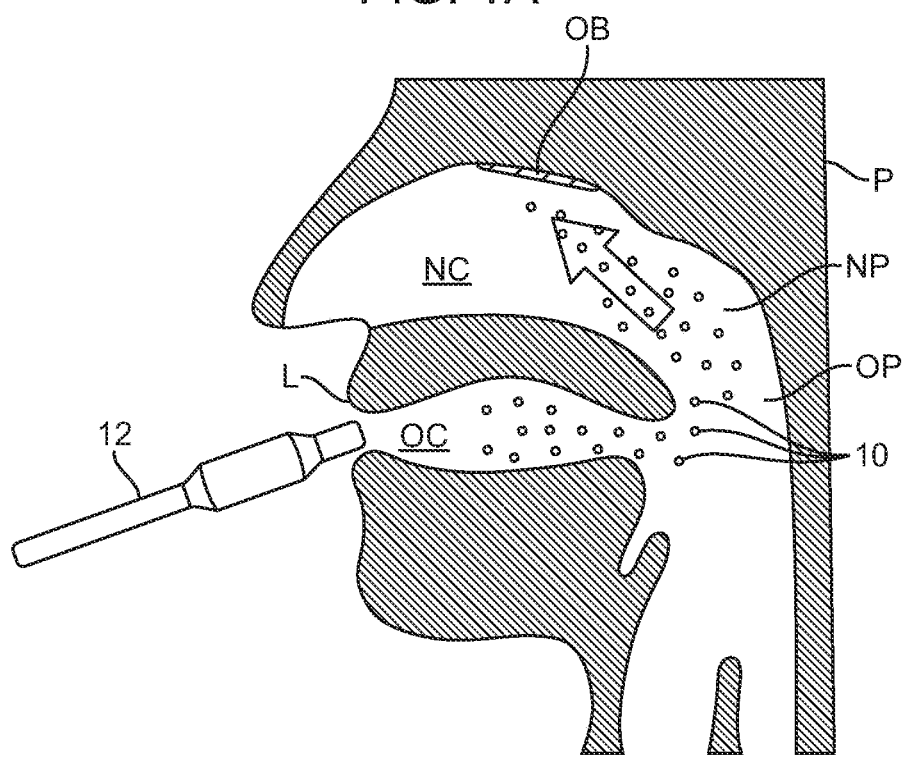
FIG. 1B illustrates a retronasal delivery route to deliver the volatiles via the oral cavity.

FIGS. 1A-1B illustrate example methods of delivery of coffee-derived volatiles 10 to a user or patient P according the present invention. Both FIG. 1A and FIG. 1B illustrate delivery of coffee-derived volatiles 10 to an olfactory bulb OB within a nasal cavity NC of the patient P. In these embodiments, the coffee-derived volatiles 10 are provided by a delivery device 12 which is positioned in relation to the patient P to allow olfactory stimulation by the coffee-derived volatiles 10 upon its delivery. It may be appreciated that the delivery device 12 may have a variety of forms, examples of which will be described in later sections. FIG. 1A illustrates an "orthonasal" delivery route in which the delivery device 12 is positioned to deliver the volatiles 10 via the nose N. Thus, a portion of the device 12 is positioned near, against, within or through one or more nostrils NO for inhalation to the nasal cavity NC and olfactory bulb OB. FIG. 1B illustrates a "retronasal" delivery route in which the delivery device 12 is positioned to deliver the volatiles 10 via the mouth or oral cavity OC. Thus, a portion of the device 12 is positioned near, against or between the lips L for delivery through the oral cavity OC, up the oropharynx OP and nasopharynx NP, to the nasal cavity NC and olfactory bulb OB. It may be appreciated that in some embodiments, the delivery device 12 is positionable within the oral cavity OC.

FIG. 2A illustrates patient P having the coffee-derived volatiles 10 delivered to the nasal cavity NC and olfactory bulb OB. FIG. 2B is a close-up illustration of a portion of the olfactory bulb OB. The olfactory bulb OB contains axons of olfactory receptor cells ORC which extend through the olfactory epithelium OE to the nasal cavity NC where the coffee-derived volatiles 10 reside. The coffee-derived volatiles 10 stimulate the receptor cells ORC. As the axons of the olfactory receptor cells ORC leave the olfactory epithelium OE, they coalesce to form a large number of bundles that together make up the olfactory nerve ON which extends to the brain B where the olfactory information is processed. Once the receptor cells ORC detect the volatiles 10, the olfactory information is sent to the brain B which identifies the smell. It is known that there are more smells in the environment than there are receptors, and any given scent molecule or volatile may stimulate a combination of receptors, creating a unique representation in the brain B. These representations are registered by the brain B as a particular smell. However, some substances and volatiles have a greater impact on the brain B than simply scent identification. It is known that certain substances, such as recreational drugs, are able to stimulate the brain reward system.

Brain Reward System

The brain reward system is a collection of brain structures and neural pathways that are responsible for reward-related cognition, including associative learning, incentive salience (i.e., motivation and desire or craving for a reward), and positive emotions, particularly emotions that involve pleasure. The brain structures that compose the reward system are located primarily within the cortico-basal ganglia-thalamo-cortical loop. This includes the mesolimbic pathway. The mesolimbic pathway is a dopaminergic pathway in the brain B. The pathway connects the ventral tegmental area VTA, which is located in the midbrain, to the nucleus accumbens NA and olfactory tubercle, which are located in the ventral striatum. The ventral tegmental area VTA projects to the nucleus accumbens NA via the medial forebrain bundle. The ventral tegmental area VTA includes a high number of dopamine neurons which are activated by the stimulated neurons in the olfactory bulb OB. Such activation causes dopamine levels in the nucleus accumbens NA to rise along with an increase of dopamine in the prefrontal cortex.

Within the brain B, dopamine functions partly as a "global reward signal", where an initial phasic dopamine response to a rewarding stimulus encodes information about the salience ("want"), value, and context of a reward. The function of dopamine varies in each axonal projection from the ventral tegmental area VTA and substantia nigra; for example, the ventral tegmental area VTA-nucleus accumbens NA shell projection assigns incentive salience to rewarding stimuli and its associated cues, the ventral tegmental area VTA-orbitofrontal cortex projection updates the value of different goals in accordance with their incentive salience, the ventral tegmental area VTA-amygdala and ventral tegmental area VTA-hippocampus projections mediate the consolidation of reward-related memories, and both the ventral tegmental area VTA-nucleus accumbens NA core and substantia nigra-dorsal striatum pathways are involved in learning motor responses that facilitate the acquisition of rewarding stimuli. Some activity within the ventral tegmental area VTA dopaminergic projections appears to be associated with reward prediction as well.

All addictive drugs directly or indirectly affect dopamine neurotransmission in the nucleus accumbens NA. The nucleus accumbens NA is well known to mediate the reinforcing effects of drugs, but more recent research emphasizes the role of the striatum as a whole, including the shell and core components of the nucleus accumbens NA and the dorsal striatum, in the processes leading first to drug abuse and then to addiction. Additional neural structures involved in different aspects of hedonic responses include the subgenual cingulate and the septal-hypothalamic areas, the amygdalar complex and other basal forebrain and brainstem structures, as well as their interconnecting pathways. Dopamine neurotransmission is also affected in many other types of pleasurable experiences—such as sex, enjoying food, or playing video games—wherein dopamine release is increased.

Stimulation of Brain Reward System with Coffee-Derived Volatiles

It has been discovered that particular types and quantities of coffee-derived volatiles 10 are able to stimulate the brain reward system in a similar manner when delivered to the olfactory bulb OB. This was achieved by measuring the brain reward system response in patients, by functional magnetic resonance imaging (fMRI), to controlled inhalation of coffee-derived volatiles 10. It was found that areas of pleasure (brain reward system) such as the ventral tegmental area VTA, the nucleus accumbens NA and amygdala are strongly stimulated by coffee-derived volatiles 10, particularly from freshly ground coffee. In addition, other cortical and basal forebrain structures were stimulated, such as the anterior cingulate cortex, the orbital prefrontal cortex, the dorsal striatum, the ventral pallidum, subgenual and septo-hypothalamic area, the dorsal striatum (left and right caudate nuclei, right putamen), and dorsal midbrain. In addition, the left amygdala and hippocampus were also activated. The nucleus accumbens NA activation showed surprising robustness (T=7.67), being the strongest statistical effects despite the fact that it generally shows lower signal to noise in functional MRI studies, indicating that the coffee aroma, presented in a phasic fashion, is especially capable of recruiting the brain reward system with an unexpected potency, and this was associated with intense feelings of pleasure. This suggests that coffee-derived volatiles 10 seem to cause not only olfactory impact but far more sophisticated effects in humans.

These fMRI studies involved twenty-three right-handed volunteers (11 men), representative of the consumer population. It is known that human olfactory perception can be measured using psychophysical tools or more complex odor generating devices systems, namely olfactometers. Thus, a computer-controlled bi-rhinal olfactometer based on air dilution was employed to deliver odor stimuli for experimental purposes. The olfactometer was used in combination with a 3.0 Tesla MRI-scanner (Philips Achieva) to measure brain activity in response to coffee-derived volatiles, as well as other scents. Two quality levels of coffee samples (specialty and commercial coffees) were employed in two quantities (1 g and 10 g of ground coffee per vial; these amounts derived from piloting experiments showing that these relative amounts were associated with a two-fold difference in perceived aroma intensity). Neutral soap was employed as a control, "neutral condition" for the fMRI experiments. Green coffee beans were subsequently roasted and ground. The sample names were coded as follows:
  a. "A" for specialty coffee
  b. "B" for commercial coffee
  c. "H" for the higher smell intensity (higher quantity of coffee; 10 g)
  d. "L" indicated lower smell intensity (lower quantity of coffee, 1 g)
  e. "N" for neutral soap The fMRI experiments, which lasted approximately 45 min (inside the MRI scanner), were performed on a 3.0 Tesla MR-scanner (Philips Achieva). The onset of odor stimulation was visually instructed (via a projected image on a computer screen that was visible to the participant via a head coil-mounted mirror) and after a 2.5 second stimulation period, the odor was rated using a button box for both pleasantness intensity and smell intensity (separately), using visual rating scales ranging from 1 (very unpleasant or very weak) to 5 (very pleasant or very intense). Each flask (vial) containing the odorant stimulus was connected by its own Teflon tube to a delivery nozzle placed within 1 cm of the nose of the participant to minimize dead space. The delivery nozzle provided stimuli to each nostril, thus producing bi-rhinal stimulation.

The behavioral data was statistically evaluated by repeated measures analysis of variance (ANOVA) with means comparison (Tukey Test). ANOVA showed that the specialty coffee had significantly ($p<0.05$) higher acceptance, being reported as highly pleasant ($4.11\pm0.66$) in the hedonic scale, while commercial coffee was perceived as not so pleasurable ($3.15\pm1.16$).

Neuroimaging data were pre- and post-processed with SPM12 software using randomized group effect analysis. SPM12 software is a major update to the SPM software, containing substantial theoretical, algorithmic, structural and interface enhancements over previous versions. Statistical Parametric Mapping (SPM) refers to the construction and assessment of spatially extended statistical processes used to test hypotheses about functional imaging data. These ideas have been instantiated in software that is called SPM. The SPM12 software package has been designed for the analysis of brain imaging data sequences. The sequences can be a series of images from different cohorts, or time-series from the same subject. The current release is designed for the analysis of fMRI, PET, SPECT, EEG and MEG.

Figure 3:
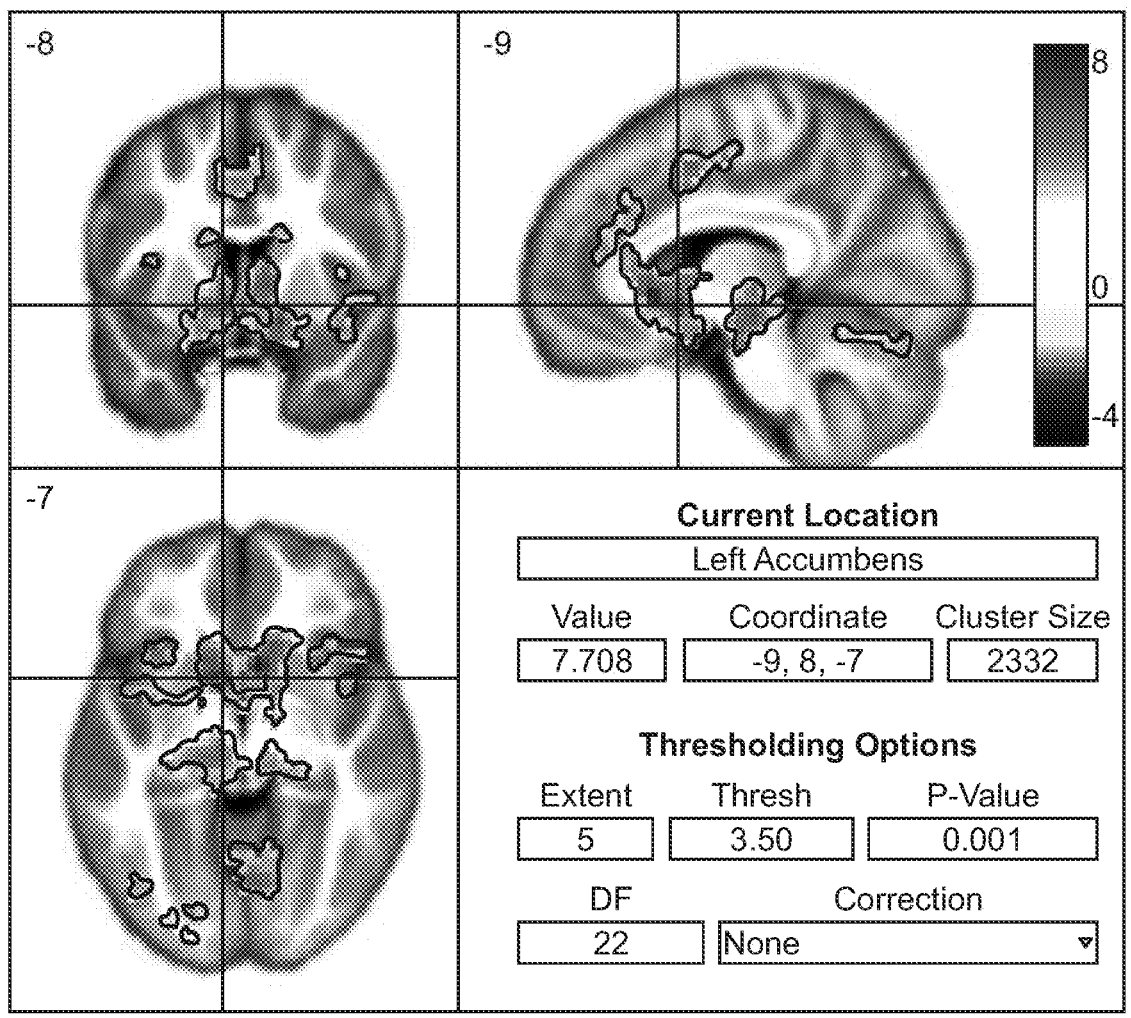
FIGS. 3-4 depicts high (AH) vs. Neutral (N) condition in an MRI Image showing robust activations in the brain reward system.
Figure 4:
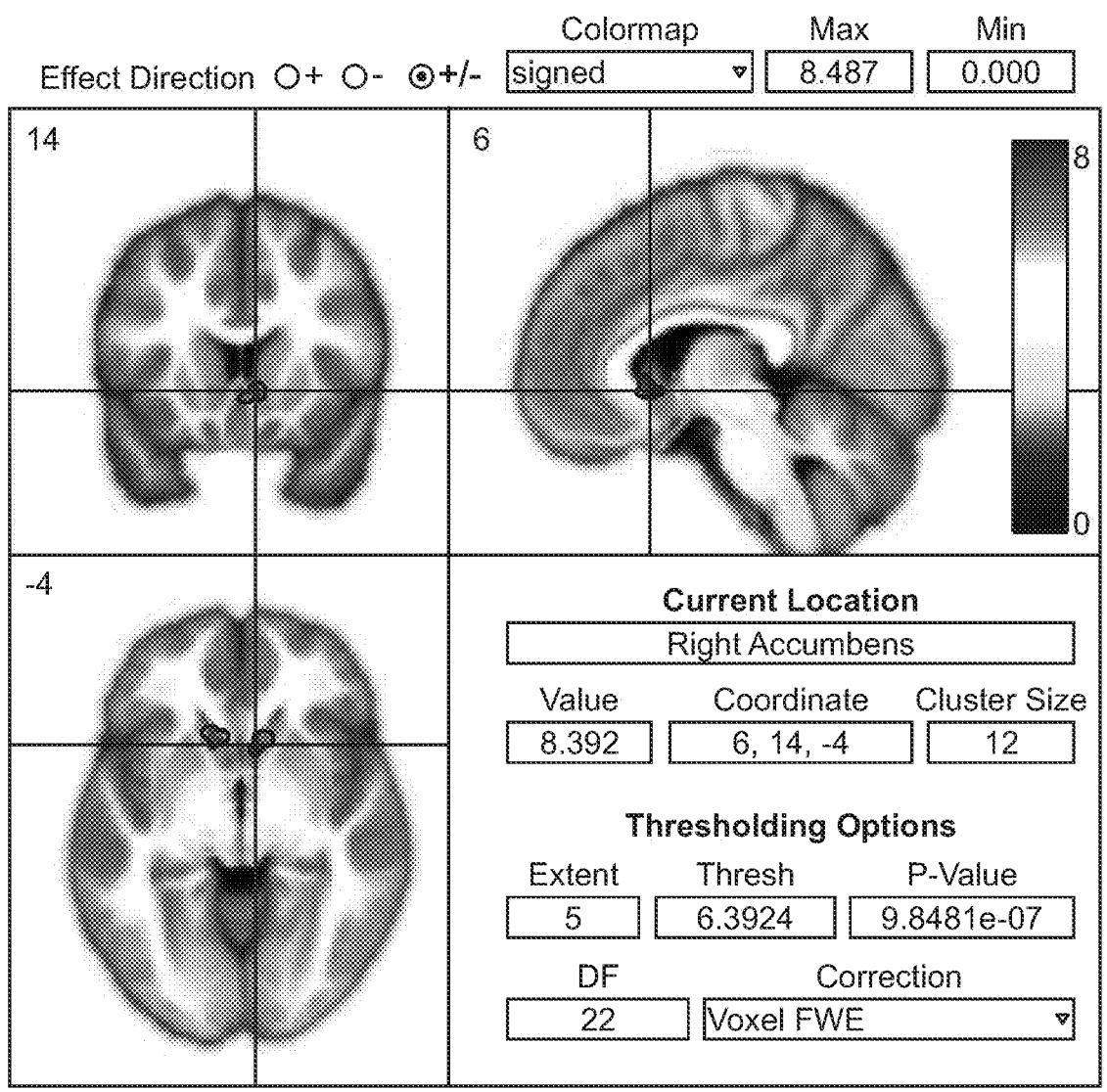

FIGS. 3-4 depict high (A-specialty coffee/H-high concentration) vs. Neutral (N) condition in an MRI Image showing robust activations in the brain reward system at significance level Z=7, 7 ($P<0.001$ uncorrected). Functional Magnetic Resonance Imaging (fMRI) statistical maps show the effect of specialty coffee aroma (A) in high concentration, including an activation of the nucleus accumbens (possibly via indirect D2 and enkephalin system stimulation), among other brain regions, associated with pleasurable responses. FIGS. 3-4 depict AH-N (using strict, family-wise discovery error correction, statistical thresholds correcting for multiple comparisons at the whole brain level) activity in the AH>N contrast in a region in the nucleus accumbens that survived whole-brain family-wise-error correction ($P<0.001$). FIGS. 3-4 show middle activation effect on the 23 volunteer participants during inhalation of specialty coffee with higher smell intensity compared to neutral (soap fragrance) inhalation. Results are statistically corrected at the whole brain level for multiple comparisons (p=0.001, family-wise discovery rate correction).

Effects were thresholded at p<0.001 corrected whole-brain FWE with a cluster criterion of five voxels. Very robust activations were observed in nucleus accumbens NA and ventral tegmental area VTA, part of the brain reward system, in addition to other cortical and basal forebrain structures such as the anterior cingulate cortex, the orbital prefrontal cortex, the dorsal striatum, the ventral pallidum, subgenual and septo-hypothalamic area, the dorsal striatum (left and right caudate nuclei, right putamen), and dorsal midbrain. In addition, the left amygdala and hippocampus were also activated. The nucleus accumbens NA activation showed surprisingly robustness (T=7.67), being the strongest statistical effects despite the fact that it generally shows lower signal to noise in fMRI studies, indicating that the coffee-derived volatiles 10, presented in a phasic fashion, are especially capable of recruiting the brain reward system with an unexpected potency, and this was associated with intense feelings of pleasure.

The results point to the fundamental brain structures of the neural circuits associated with the reward and motivation system. This holds for comparisons between:
  a. coffee versus neutral contrasts
  b. coffee A versus coffee B
  c. coffee H versus L
  d. coffee A/H versus neutral
  e. the interaction between quality and intensity (A/H−A/L)−(B/H−B/L); results were highest when pleasantness intensity and smell intensity were each in the range of 3-5.

This suggests that the olfactory system has strong links with circuits involved in emotion and hedonism. For coffee B versus coffee A and coffee L versus coffee H contrasts, the same was not observed. These results are compatible with the behavioral data of the scales and with the fact that specialty coffee is generally more appreciated than commercial coffee.

Activation at the nucleus accumbens showed surprisingly robust activation with the highest statistical effects, despite the fact that in functional magnetic resonance studies, its signal is in general lower than noise. This indicates that coffee aroma is especially capable of recruiting the brain reward system with an unexpected power, which was associated with intense feelings of pleasure.

Thus, the human brain reward system, measured by functional magnetic resonance imaging (fMRI), responded phasically and with unexpected potency (comparable to stimulant drugs such as cocaine, nicotine, etc) to inhaled coffee-derived volatiles 10, especially when high quality coffee beans were employed. Consequently, a variety of methods of controlled inhalation of coffee-derived volatiles 10 is provided to stimulate the human brain reward system, particularly causing olfactory stimulation of a ventral tegmental area VTA neuron or a nucleus accumbens NA neuron in an intensity comparable to stimulant drugs. The nucleus accumbens NA and the ventral tegmentum are the primary sites where addictive drugs act. The following are commonly considered to be addictive: heroin, cocaine, alcohol, opiates, nicotine, amphetamine, and their synthetic analogs. These drugs alter the neuromodulatory influence of dopamine on the processing of reinforcement signals by prolonging the action of dopamine in the nucleus accumbens NA or by stimulating the activation of neurons there and also in the ventral tegmental area VTA. The most common drugs of abuse stimulate the release of dopamine, which creates both their rewarding and the psychomotor effects. Compulsive drug-taking behaviors are a result of the permanent functional changes in the mesolimbic dopamine system arising from repetitive dopamine stimulation. Molecular and cellular adaptations are responsible for a sensitized dopamine activity in the ventral tegmental area VTA and along the mesolimbic dopamine projection in response to drug abuse. These alterations in neural processing could account for the waning influence of adaptive emotional signals in the operation of decision making faculties as drug-seeking and drug-taking behaviors become habitual and compulsive. The withdrawal phenomenon occurs because the deficit in reward functioning initiates a distress cycle wherein the drugs become necessary to restore the normal homeostatic state.

In addition, a clinical trial was undertaken wherein four smokers participated in a scientific study approved by an Ethics Committee to evaluate if a delivery device according to the present invention was able to reduce the desire to smoke. One of the ways to measure the effect of some intervention on cigarette addiction is through the use of craving scales before and after intervention. To that end, the participant responded to the Questionnaire of Smoking Urges-Brief (QSU-B, Araujo et al., 2007). QSU-B is a craving rating scale composed of 10 affirmative questions:
  a. Question 1: I want to smoke a cigarette now.
  b. Question 2: Nothing would be better than smoking a cigarette now.
  c. Question 3: If it were possible, I would probably smoke now.
  d. Question #4: I would control things better if I could smoke now.
  e. Question #5: All I want is to smoke a cigarette.
  f. Question 6: I need a cigarette now.
  g. Question 7: Smoking a cigarette would be nice at this moment.
  h. Question 8: I would do just about anything for a cigarette now.
  i. Question 9: Smoking would make me less depressed.
  j. Question 10: I will smoke as soon as possible.

The participant answers to the questionnaire using a likert scale of 7 points from "totally disagree" to "strongly agree". In addition, it was also evaluated how pleasant the aroma was perceived (pleasantness intensity) and how intense the aroma was perceived (smell intensity).

The QSU-B was analyzed by means of the sum of total of points, points of factor 1, points of factor 2, and points of categories 1-4 which have the following correlations:
  a. [QSB-U 1° FT1] factor 1 (questions 1, 3, 7 and 10)—before inhalation
  b. [QSB-U 2° FT1] factor 1 (questions 1, 3, 7 and 10)—after inhalation
  c. [QSB-U 1° FT2) factor 2 (questions 4, 8 and 9)—before inhalation
  d. [QSB-U 2° FT2) factor 2 (questions 4, 8 and 9)—after inhalation
  e. [QSB-U 1° C1] Category 1—Desire to smoke (questions 1, 5 and 6)—before inhalation
  f. [QSB-U 2° C1] Category 1—Desire to smoke (questions 1, 5 and 6)—after inhalation
  g. [QSB-U 1° C2] Category 2—Anticipation of positive effect (questions 2 and 7)—before inhalation
  h. [QSB-U 2° C2] Category 2—Anticipation of positive effect (questions 2 and 7)—after inhalation
  i. [QSB-U 1° C3] Category 3—Relief of withdrawal symptoms or negative effect (questions 4 and 9)—before inhalation j. [QSB-U 2° C3] Category 3—Relief of withdrawal symptoms or negative effect (questions 4 and 9)—after inhalation
k. [QSB-U 1° C4] Category 4—Intention of smoking (questions 3, 8 and 10)—before inhalation
l. [QSB-U 2° C4] Category 4—Intention of smoking (questions 3, 8 and 10)—after inhalation The craving variations, in the different abstinence times, were measured by the total QSU-B score, QSU-B 1° ST (before inhalation) and QSU-B 2° ST (after inhalation). The results are provided in Table 1.

TABLE 1

Craving variations according to Questionnaire of Smoking Urges-Brief (QSU-B).

| Participant | QSU-B_1° ST | QSU-B_2° ST | QSB-U 1° FT1 | QSB-U 2° FT1 | QSB-U 1° FT2 | QSB-U 2° FT2 | QSB-U 1° C1 | QSB-U 2° C1 | QSB-U 1° C2 | QSB-U 2° C2 | QSB-U 1° CT3 | QSB-U 2° CT3 | QSB-U 1° CT4 | QSB-U 2° CT4 |
|---|---|---|---|---|---|---|---|---|---|---|---|---|---|---|
| S1 | 63 | 60 | 23 | 23 | 20 | 20 | 20 | 20 | 10 | 7 | 13 | 13 | 20 | 20 |
| S2 | 56 | 46 | 22 | 18 | 20 | 17 | 19 | 16 | 8 | 4 | 13 | 11 | 16 | 15 |
| S3 | 34 | 30 | 14 | 13 | 14 | 14 | 11 | 8 | 2 | 2 | 8 | 8 | 13 | 12 |
| S4 | 50 | 48 | 22 | 20 | 16 | 16 | 17 | 17 | 7 | 5 | 9 | 9 | 17 | 17 |

Comparing the values of scales applied before and after the intervention, it can be observed that craving either remained stable or diminished, thus showing the effectiveness of the utilization of the delivery device in reducing symptoms.

It is provided that the controlled inhalation of particular coffee-derive volatiles 10 can be used to treat addiction to stimulant drugs by providing a similar stimulatory effect in the brain B. However, unlike stimulant drugs, the inhalation of coffee-derive volatiles 10 does not have detrimental physical side effects, such as heart rate irregularities and risk of heart attack, respiratory problems such as lung cancer, emphysema and breathing problems, abdominal pain, vomiting, constipation, diarrhea, kidney and liver damage, seizures, stroke, brain damage, and potential death. Likewise, inhalation of coffee-derive volatiles 10 does not have detrimental psychological side effects such as exaggerated mood swings, depression, anxiety, paranoia, violence, decrease in pleasure in everyday life, complication of mental illness, hallucinations, confusion and psychological tolerance to the substance's effects creating a desire to receive ever-increasing amounts of the substance.

In addition, the coffee-derive volatiles 10 are not carcinogenic and are considered safe; large-scale studies on coffee consumption are available, coffee beans are widely used and no restrictions from the United States Food and Drug Administration currently apply in handling or smelling coffee. Unlike smoking of tobacco and other substances that involve heating, coffee-derived volatiles 10 may be delivered to the patient without the use of heat. This avoids artifacts related to the heating process and reduces the risks of generating a number of toxic compounds commonly produced when heating organic and inorganic substances. Thus, no byproducts are formed, and no additional substances, stabilizers or physical processes such as heating are required at the point of delivery to the patient.

Coffee Substances

The volatiles 10 delivered to the patient P with the use of the delivery devices and systems described herein are all originally derived from coffee. However, the volatiles 10 may vary depending on the type of coffee beans, the processing of the beans, and any further processing, such as grinding or extraction of coffee oil.

Coffee possesses a very complex matrix in terms of component aromas. Freshly roasted coffee beans, especially when recently grinded, reveal strong and pleasant smells. They can yield nearly a thousand volatile compounds, more than any other known natural product, including herbs and flowers. These can be divided into different classes, including (in order of abundance) furans, pyrazines, ketones, pyrroles, phenols, hydrocarbons, acids and anhydrides, aldehydes, esters, alcohols, sulfur compounds, and others. It is believed, however, that only about 5% of these compounds are actually odorous and capable of impacting coffee aroma.

Among these compounds, pyrazines stand out, followed by furans, aldehydes, ketones, phenols and sulphur compounds, among others.

Aromas that are perceived in roasted coffee generally derive from a combination of at least a few related molecules. The synergism among related molecules occurs when each odor compound has a unique threshold concentration, above which it is perceived and interacts with the other ones. The aroma profiles thus depend on a complex interaction of different molecules and their relative concentration. Therefore, even though some compounds may have high impact (compounds that possess high odor activity in isolation) these may not necessarily be the ones contributing to the aroma perception and subjective experience.

It is known that high-quality and low-quality coffee seeds exhibit distinct aroma profiles. The sensory quality of coffee brew is strictly related to the chemical composition of raw seeds and post-harvest processing conditions (especially roasting). The most important criteria employed worldwide in coffee trading is the cup quality and presence of defective seeds and of strange matters.

The quality of green coffee beans is a result of a complex interaction of climate and soil and coffee genotypes, different crop management systems, harvest type and time, cherry quality and processing, bean storage, its transportation, and finally, the roasting process. Specialty coffee is based on the plant species *Coffea arabica* L. (*Arabica*). *Coffea arabica* fruits developed at higher altitudes can produce more mucilage and they can be richer in sugars and other soluble solids. The fruits are grown under near-perfect conditions and processed very carefully. The coffee beans are roasted in small batches to find the ideal flavor profile. Thus, specialty coffee is higher quality, having a more refined aroma and a distinct sweet and floral/fruity flavor. Although commercial coffee may also be based on the plant species *Coffea arabica* L. (*Arabica*), the coffee is of lower quality and made of coffee beans with defects, stones, sticks, broken beans, chipped beans and beans damaged by insects.

After the coffee cherries have been selectively picked or mechanically separated in the process itself, they have to undergo several processing steps. One well-known technique for its capacity of producing special coffees is the wet method through a better selection of ripe and perfect fruits. In general, the coffee produced by this method is more aromatic and has less bitterness. Dry parchment coffee must be stored at moisture levels below 12% in order to avoid the development of musty, earthy or fermented flavors. However, it is the roasting process who is responsible for most of the delightful sensorial properties of coffee. Generally, most of the aroma compounds are generated at light-medium or medium roast. Darker roasts have a less volatile profile and may contain a number of unhealthy molecules.

The presence of defective seeds is detrimental ones to the aroma of the coffee. Defective seeds often have a somewhat negative character as tarry, fermented, smoky, woody, spicy, leathery or medicinal, acrid, burnt, rubber odors. Whereas selected beans yield extremely pleasant smells (e.g. caramel, chocolate and nut notes).

Overall, defective seeds show higher number and concentration of volatile compounds compared to those of good seeds, including some pyrazines and pyrroles, as well as butyrolactone and hexanoic acid. These were previously regarded as potential markers of defective seeds because they were observed exclusively in defective seeds. The compounds which were suggested as potential roasted defective seeds' markers was: hexanoic acid, β-linalool, 2-butyl-3,5-dimethylpyrazine, 2-pentylfuran. Additional compounds suggested as low quality indicators were 2,3,5, 6-tetramethylpyrazine,2,3-butanediol and 4-ethylguaiacol, b-linalool, 2-,3-dimethylbutyl butanoate, 2-phenylethyl acetate, 2,3-butanedione, hexanedioic acid, guaiacol, 2,3-dihydro-2-methyl-1H-benzopyrrol, 3-methylpiperidine, 2-pentylpiperidine, 3-octen-2-one, 2-octenal, 2-pentylfuran and 2-butyl-3-methylpyrazine and phenols. Nonetheless, some of these compounds may contribute with pleasant notes when in low concentrations. Thus, in preferred embodiments, specialty coffee, having a lower frequency of defective seeds and other contaminants, is used as the coffee substance of choice. In addition, light-medium roast is desired.

Two primary dimensions can be used to characterize subjective emotional responses in the context of stimulus evaluation: intensity and valence. Although in principle they are expected to independently contribute to subjective experience, intensity and valence are often asymmetrical and may interact with each other. Intensity and valence are often correlated within the evaluative space. A pleasant or an aversive stimulus typically becomes more pleasant or unpleasant as they become more intense. In the case of coffee aroma, these observations seem to hold, but some caveats are worth mentioning. For some people, even the smell of lower quality coffee ("commercial" coffee) in high concentrations can be experienced as pleasant. Strong smells of coffee are a very important characteristic for consumer acceptance.

Another intriguing feature of coffee is that the beverage never seems to taste as good as it smells. Actually, the pleasant sensation of smelling freshly ground coffee beans (at least at a short distance) is overall stronger than smelling the rather weaker aroma exhaling from a cup of coffee. There are two reasons for this: (1) recently grinded coffee has more volatiles than the aroma of a cup of percolated coffee, regardless of the brewing methods chosen (this is mainly because not all volatiles are extracted to the beverage); (2) the act of swallowing the drink sends a burst of aromas up the back of the nose from inside the mouth, activating a "second sense of smell", as known as retronasal perception, which is less powerful in terms of flavour, and therefore less satisfying. This happens because, in the case of coffee, the flavor perception is partially hampered by the fact that molecules that combine to form coffee's complex aroma are wiped out by saliva, causing the flavor to change during the swallowing process. In fact, the sense of olfaction is the only one that has a "double nature"—that is, it can be perceived from the outside (orthonasal perception) or from inside the mouth (retronasal perception).

In specific embodiments, the invention can be performed by enclosing a coffee substance, such as whole coffee beans, ground coffee, coffee oil with or without additives, single or mixed coffee molecules, each from natural or synthetic sources or any combination of these, to name a few, in an inhalation device or delivery device 12 that allows a user to inhale volatiles 10 released from the coffee substance via an orthoonasal and/or retronasal delivery route. In other embodiments, the coffee substance may be further prepared and/or combined with other active and/or inactive substances and carriers to enhance, control, or otherwise affect the delivery, activity, uptake or other characteristics of the coffee volatiles. In embodiments where the coffee substance includes ground coffee, it is preferred that the coffee be ground shortly before use, e.g. less than six hours before use, preferably less than one hour before use, often less than 30 minutes before, and usually less than 15 minutes before use, as the effective aromatic volatiles are labile and can be lost if the ground coffee is exposed to the atmosphere for extended time periods before use. Alternatively, the ground coffee may be preserved in a sealed package or container. For example, the ground coffee may be formed as an ultra-concentrated stabilized coffee powder with enhanced freshness aroma retention, but such preservation techniques are generally less preferred.

In some embodiments, 10 g of coffee substances are disposed within the delivery device 12. However, it may be appreciated that other quantities may alternatively be used, including 1 g, 2 g, 3 g, 4 g, 5 g, 6 g, 7 g, 8 g, 9 g, 9.5 g, 10 g, 10.5 g, 11 g or more. Similarly, quantities such as 0.04-18 g, 1-10 g, 5-10 g, 9-11 g, 9.5-10.5 g, may be used. Likewise, quantities less than 1 g may also be used, including 0.5 g and 0.25 g. Such quantities may differ depending on the type of coffee substance used (e.g. species of coffee, type of processing, degree of roasting, degree of grinding, ground coffee vs. coffee oil, etc.) and/or on the desired effect.

Dosages

It may be appreciated that in most embodiments, the delivery device 12 provides coffee-derived volatiles 10 in the form of a dose. Typically, a single dose is that which is sufficient to cause olfactory stimulation of the brain reward system, such as the ventral tegmental area or nucleus accumbens, in a high intensity, such as an intensity equivalent to an addictive or recreational drug. Thus, the user is able to obtain the same or similar effect from a dose of coffee-derived volatiles 10 that the user would obtain from the use of an addictive drug, thereby allowing the user to eliminate usage of the addictive drug and its detrimental side effects.

It may be appreciated that a dose of coffee-derived volatiles 10 may be provided to the user with a single actuation of the delivery device 12 or a plurality of actuations within a short time period. Such delivery is to be phasic, wherein a dose is provided to the user in a short time period or phase and then not provided to the user therebetween. For example, the volatiles 10 may be delivered over seconds or minutes and then delivered again hours or days later. For example, volatiles 10 may be delivered over 1-2 minutes and then delivered again 2-3 hours later. Such dosing triggers dopamine spikes without the tolerance observed in drug consumption such as nicotine and other psychoactive substances.

A chemical study was undertaken to determine an example of specific coffee-derived volatiles 10 from a coffee substance sample used in the present invention. The powdered coffee substance sample of the fMR analysis (described above) was used for the chemical analysis. The powdered coffee substance sample was contained in the fMRI vial sealed with a plastic cap and silicone septum. Headspace-Solid Phase Micro Extraction (HS-SPME) extractions were carried out using 10 g of the powdered coffee substance sample and a Divinylbenzene/Carboxen/Polydimethylsiloxane (DVB/CAR/PDMS) (50/30 µm) fiber (Supelco Analytical, Supelco is a part of the Sigma-Aldrich Corporation). In Solid Phase Micro Extraction (SPME), analytes can be adsorbed from a solid sample, by headspace extraction, using a polymer-coated fused silica fiber. Analytes are desorbed from the fiber by exposing the fiber in the injection port of a gas chromatograph (GC) or in the desorption chamber of a Solid Phase Micro Extraction (SPME)/High-Performance Liquid Chromatography (HPLC) interface.

The volatile fraction extraction method was adapted from Amaral et al., 2017 and had an equilibration time of 20 min and an extraction time of 30 min. Heating at 35° C. was made in an Agilent 6890N GC oven. HS-SPME extractions of n-alkanes were performed with the same fibre in order to determine the LRI [17] of the substances identified in the sample. The volatile fractions were analysed using an Agilent 7820A-5977E GC-MS system, with the same columns and the same chromatographic conditions as for the standards. However, the SPME injections were performed manually, in splitless mode, by desorbing the fibre in the injector at 250° C. for 1 min (sample) and 0.2 min (n-alkanes). A SPME liner with an internal diameter of 0.75 mm (Supelco) was used. After the injection time, the fibre remained for a further 4 min in the injector to ensure complete cleaning.

The composition of the coffee volatile fraction present in the headspace identified by GCMS and quantified by GC-FID is presented in Table. 2.

TABLE 2

Composition of the coffee volatile fraction present in the headspace identified by GCMS and quantified by GC-FID.

| Molecules | Coffee TR | m (µg) | m (µg) |
|---|---|---|---|
| acetaldehyde | 1,584 | 27.53 | 51.14 |
| 2-methyl-furan | 2,149 | 134.34 | 256.14 |
| 2-butanone | 2,356 | 68.44 | 141.61 |
| 2-methyl-butanal | 2,449 | 53.52 | 228.36 |
| 3-methyl-butanal | 2,473 | 16.80 | 143.18 |
| 2,5-dimethyl-furan | 2,782 | 30.14 | 65.43 |
| 2,3-Butanedione | 3,017 | 38.09 | 124.78 |
| 3-Hexanone | 4,175 | 112.10 | 265.58 |
| 2-vinyl-furan | 4,418 | 15.71 | 39.15 |
| Hexanal | 4,604 | 9.44 | 32.77 |
| 2,3-Hexanedione | 5,612 | 20.84 | 38.40 |
| 1-methyl-1H-pyrrole | — | 32.55 | 71.91 |
| 3-methyl-phenol | 6,179 | 25.95 | 46.10 |
| pyridine | 7,135 | 342.99 | 667.70 |
| 2-(2-propenyl)-furan | 7,708 | 7.88 | 21.46 |
| pyrazine | 7,891 | 3.70 | 79.80 |
| 2-(methoxymethyl)-furan | 8,675 | 12.68 | 20.34 |
| dihydro-2-methyl-3(2H)-furanone | 9,512 | 87.98 | 206.18 |
| methyl-pyrazine | 9,651 | 371.18 | 701.13 |
| 1-hydroxy-2-propanone | 10,729 | 42.67 | 73.22 |
| 2,5-dimethyl-pyrazine | 11,639 | 96.27 | 225.59 |
| 2,6-dimethyl-pyrazine | 11,871 | 104.02 | 232.28 |
| ethyl-pyrazine | 12,012 | 55.89 | 121.28 |
| 2-methyl-3-pentanol | 12,245 | 17.54 | 37.06 |
| 2,3-dimethyl-pyrazine | 12,466 | 18.69 | 44.35 |
| 2-Cyclopenten-1-one | 12,643 | 5.16 | 9.27 |
| Isopropyl Alcohol | 12,867 | 16.24 | 32.31 |
| 2-methyl-2-cyclopenten-1-one | 13,129 | 6.67 | 12.90 |
| 1-Hydroxy-2-butanone | 13,388 | 15.88 | 28.54 |
| 3-ethyl-pyridine | 13.81 | 2.33 | 4.32 |
| 2-ethyl-6-methyl-pyrazine | 13,946 | 27.39 | 64.49 |
| 2-ethyl-5-methyl-pyrazine | 14,167 | 20.42 | 46.33 |
| trimethyl-pyrazine | 14,699 | 34.83 | 75.41 |
| 2-(n-propyl)-pyrazine | 15,109 | 1.28 | 2.81 |
| 2-furfurylthiol | 15,583 | 3.92 | 8.11 |
| ethenyl-pyrazine | — | 6.04 | 13.70 |
| 1-Hydroxy-2-pentanone | 16,035 | 2.84 | 4.61 |
| 3-ethyl-2,5-dimethyl-pyrazine | 16,288 | 38.96 | 78.68 |
| acetic acid | — | 67.21 | 129.40 |
| furfural | 16,758 | 114.71 | 233.23 |
| 1-(acetyloxy)-2-propanone | 17,049 | 114.21 | 216.18 |
| 1-(2-methyl-1-cyclopenten-1-yl)-ethanone | 17,163 | 3.32 | 7.67 |
| 2-[(methylthio)methyl]-furan | 17,581 | 4.11 | 8.95 |
| 2-ethenyl-6-methyl-pyrazine | 17,751 | 2.55 | 6.16 |
| furfuryl formate | 18,118 | 29.84 | 62.25 |
| 1-(2-furanyl)-ethanone | 18,315 | 59.05 | 122.97 |
| benzaldehyde | 18,779 | 17.38 | 33.38 |
| furfuryl isothiocyanate | 18,931 | 10.67 | 23.28 |
| dihydro-2-methyl-3(2H)-thiophenone | 19,041 | 3.25 | 7.15 |
| tetramethyl-pyrazine | 19,201 | 2.65 | 6.25 |
| furfuryl acetate | 19,761 | 93.42 | 212.32 |
| propanoic acid | 19,841 | 15.92 | 25.99 |
| 2,3-butanediol | 20,169 | 3.60 | 7.40 |
| 3-methyl-1H-pyrrole | 20,294 | 2.90 | 5.89 |
| 5-methyl-2-furancarboxaldehyde | 20,969 | 89.00 | 201.42 |
| dihydro-3-methylene-2(3H)-furanone | 21,208 | 3.47 | 8.12 |
| 2,2'-bifuran | 21,662 | 0.59 | 20.15 |
| isopropenyl-pyrazine | 21,745 | 1.40 | 3.30 |
| 1-(2-pyridinyl)-ethanone | 21,892 | 5.86 | 13.20 |
| furfuryl propanoate | 22,011 | 4.34 | 9.62 |
| 2,2'-methylenebis-furan | 22,322 | 5.26 | 12.18 |
| 1-methyl-1H-pyrrole-2-carboxaldehyde | 22,561 | 12.33 | 27.31 |
| butyrolactone | 22,792 | 59.52 | 130.22 |
| 2,5-dihydro-3,5-dimethyl-2-furanone | 23,594 | 7.24 | 16.97 |
| 1-(1-methyl-1H-pyrrol-2-yl)-ethanone | 23,908 | 3.52 | 7.09 |
| furfuryl alcohol | 24,592 | 369.71 | 705.53 |
| 3-methyl-butanoic acid | 24,816 | 1.97 | 42.19 |
| 2-acetyl-3-methylpyrazine | 25,302 | 3.54 | 8.33 |
| N-acetyl-4(H)-pyridine | 26,261 | 2.12 | 4.99 |
| 2(5H)-furanone | 27,287 | 2.36 | 5.91 |
| 1-(2-furanylmethyl)-1H-pyrrole | 30.11 | 2.28 | 4.68 |
| 2-hydroxy-3-methyl-2-cyclopenten-1-one | 30,302 | 1.48 | 7.14 |
| 2,5-dihydro-3,5-dimethyl-2-furanone | 30,446 | 0.53 | 2.31 |
| 2-methoxy-phenol | 31.24 | 1.71 | 4.36 |
| 1-methyl-1H-pyrrole-2-carboxaldehyde | 31.34 | 0.94 | 2.16 |
| 1-(1H-pyrrol-2-yl)-ethanone | 35,012 | 0.93 | 5.88 |
| phenol | 36,181 | 1.24 | 2.74 |
| 1H-pyrrole-2-carboxaldehyde | 36,629 | 0.16 | 0.45 |
| 2-phenoxy-ethanol | 40,416 | 0.74 | 2.61 |

Figure 5:
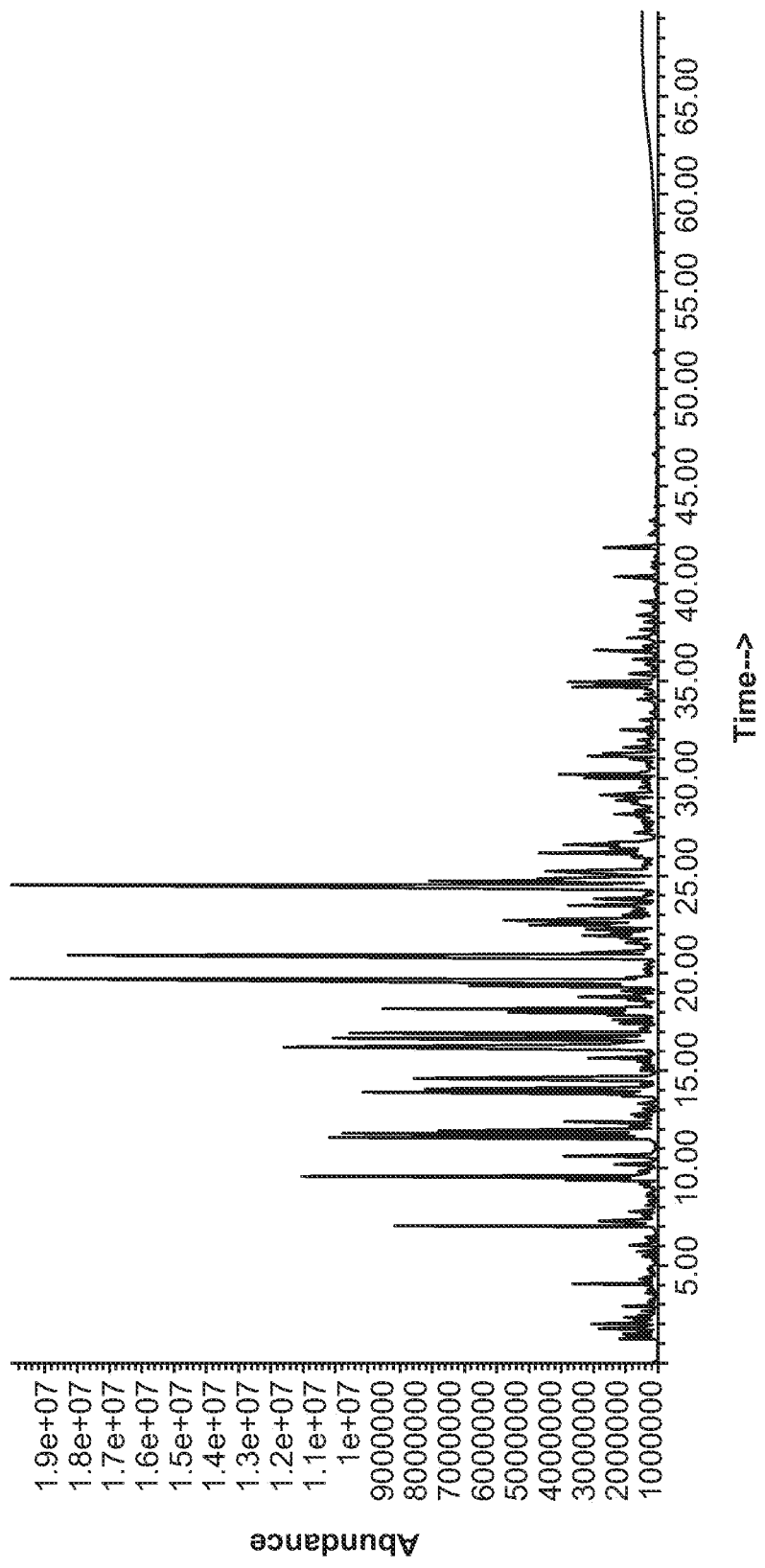
FIG. 5 provides a chromatogram showing the composition of the coffee volatiles present in the headspace identified by Gas Chromatography-Mass Spectrometry (GCMS).

FIG. 5 provides a chromatogram showing the composition of the coffee volatiles present in the headspace identified by Gas Chromatography-Mass Spectrometry (GCMS). GCMS is an analytical method that combines the features of gas-chromatography and mass spectrometry to identify different substances within a test sample.

Delivery Devices

A variety of delivery devices are provided for delivery of coffee-derived volatiles 10 to the user via a orthonasal and/or retronasal route.

Figure 6A:
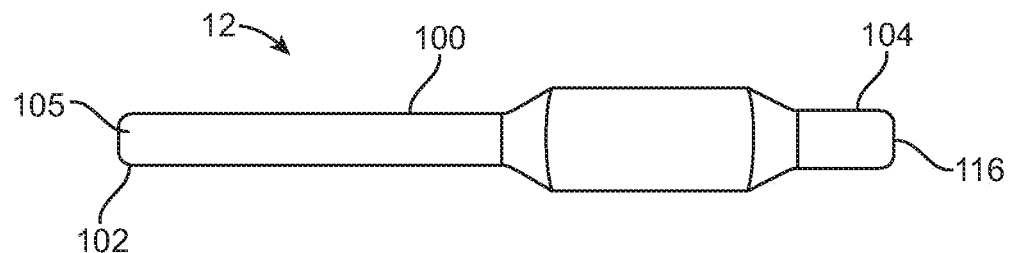
FIGS. 6A-6B illustrates an embodiment of a delivery device having an elongate shape convenient for holding in the hand of the user.
Figure 6B:
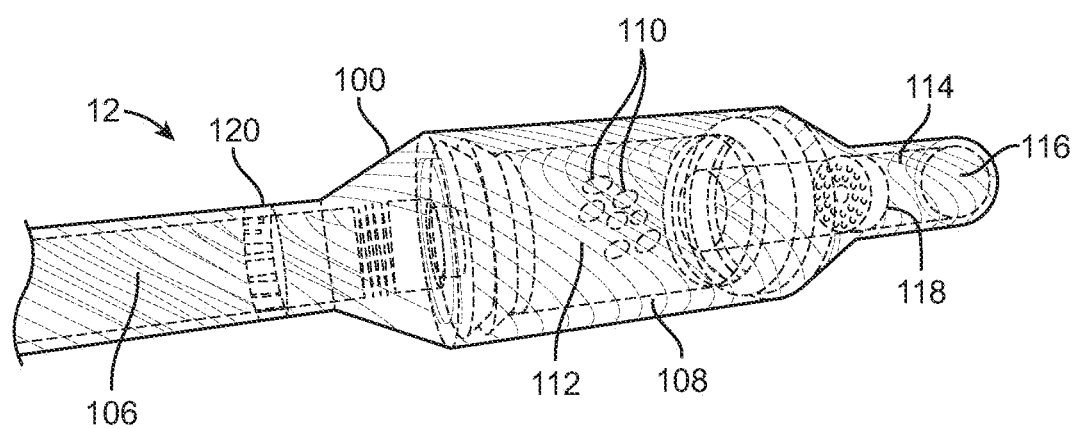

FIGS. 6A-6B illustrates an embodiment of a delivery device 12 having a housing body of an elongate shape convenient for holding in the hand of the user. It may be appreciated that the housing body may have a variety of shapes and sizes, including round, oblong, square, rectangular, cylindrical, conical, disc-shaped, and the like. In this embodiment, the delivery device 12 is approximately 103 mm long and 14 mm wide at its widest portion. which is a convenient size, but other versions with bigger or smaller dimensions and shapes are possible.

In this embodiment, the delivery device 12 comprises a housing body in the shape of an elongate shaft 100 having a first end 102 and a second end 104. In this embodiment, the first end 102 has an inlet opening 105 leading to an airway lumen 106. This allows air to flow into the delivery device 12. The airway lumen 106 leads to a chamber 108 which is configured to hold a coffee substance 110. The coffee substance 110 may comprise whole coffee beans, ground coffee, coffee oil with or without additives, single or mixed coffee molecules, each from natural or synthetic sources or any combination of these, to name a few. In some embodiments, the coffee substance 110 is further processed by the user to assist in release of coffee-derived volatiles 10 therefrom. For example, the user may grind whole coffee beans or bite or chew the ground coffee before it is inserted in the device. 12.

In some embodiments, the chamber 108 is configured to contain or receive the coffee substance 110 directly, however in this embodiment, the chamber 108 is configured to contain or receive a cartridge 112 containing the coffee substance 110. For one-time use, the delivery device 12 is typically prefilled with coffee substance 110, either directly in the chamber 108 or within a cartridge 112 housed within the chamber 108. The delivery device 12 is then disposed of after use. For multiple-use, the delivery device 12 is refillable or rechargeable. In such instances, the chamber 108 is accessible by the user for refilling with coffee substance 110. In such embodiments, the chamber 108 may include indication lines, grooves, partitions or other elements to assist in filling the chamber 108 with a desired quantity of coffee substance 110. In other embodiments, the chamber 108 is accessible by the user for exchanging the cartridge 112 therein. The use of a cartridge 112 allows for ease of refilling the delivery device 12 since the cartridge 112 contains a predetermined quantity of coffee substance 110 and can be quickly inserted into the chamber 108 while on the go. In some embodiments, the cartridge 112 is provided to the user in a pre-filled and sealed state. In other embodiments, the cartridge 112 is accessible and refillable by the user to simply allow for preparation in advance. In either case, the user may carry a plurality of cartridges 112 for later use. It may be appreciated that in some embodiments, the cartridge 112 is flexible to allow the user to crush the coffee substance 108 therein, such as by chewing or pressing on the cartridge 112, to assist in releasing the coffee-derived volatiles 10. It may also be appreciated that in some embodiments at least a portion of the elongate shaft 100 disposed around the chamber 108 may be flexible to allow the user to crush the coffee substance 108 therein, particularly when a cartridge 112 is not used.

In this embodiment, the chamber 108 is connected with a volatile lumen 114 which extends to the second end 104 and an outlet opening 116. Thus, air is carried into the delivery device 12 through the inlet opening 105 and through the chamber 108 where it picks up coffee-derived volatiles 10 from the coffee substance 110. The coffee-derived volatiles 10 are then carried through the volatile lumen 114 and out the outlet opening 116. The coffee-derived volatiles 10 are delivered to the user either orthonasally (as in FIG. 1A) or retronasally (as in FIG. 1B). Orthonasal delivery is provided by positioning the delivery device 12 near the user so that the outlet opening 116 is directed toward the nostrils NO of the nose N. In some embodiments, air movement is assisted by suctioning of air into the nostrils NO such as by sniffing or inhaling through the nose N. Retronasal delivery is provided by positioning the delivery device 12 near the user so that the outlet opening 116 is directed toward the oral cavity OC of the user. In some embodiments, air movement is assisted by sucking from the outlet opening 116 so as to draw air through the delivery device 12 and into the oral cavity OC. However, it may be appreciated that airflow may be due to natural airflow in the environment or generated by an internal airflow accelerator, such as a fan-type mechanism, within the delivery device 12. In some embodiments, the airflow accelerator is electronically controlled. In other embodiments, the airflow accelerator mechanically controlled, such as by a mechanical pumping mechanism actuated by the user.

In any case, airflow is typically actuated by the user to provide a discrete dose to the user. Each dose is sufficient to stimulate the brain reward system of the user. In particular, each dose is sufficient to stimulate the brain reward system, such as the ventral tegmental area VTA and/or nucleus accumbens NA, in an intensity equivalent to the use of addictive drugs, such as cocaine, heroin, opioids, methamphetamines or nicotine. Thus, the user is able to obtain the same or similar effect from a dose of coffee-derived volatiles 10 that the user would obtain from the use of an addictive drug, thereby allowing the user to eliminate usage of the addictive drug and its detrimental side effects.

As mentioned previously, a dose of coffee-derived volatiles 10 may be provided to the user with a single actuation of the delivery device 12 or a plurality of actuations within a short time period. Such delivery is to be phasic.

The user is able to carry the delivery device 12 in a non-use or unactuated state wherein coffee-derived volatiles 10 are not released from the device 12. Then, when desired, the user is able to actuate the device 12 to provide a dose of coffee-derived volatiles 10. Such actuation typically provides a predetermined dose of coffee-derived volatiles 10. Future doses may be delivered with a new device 12 (disposable), or the same device 12 (refillable) as needed, as desired, according to a dosing schedule, or any combination of these. Dose and dosage scheduling may depend on the purpose of using the device 12. For example, use to treat an addiction may depend on the type of addiction and/or level of addiction by the user. Doses and dosing schedules may be predetermined, such as by a physician, based on scientific data supporting methods of achieving a particular result, such as decrease in use of the addictive drug over time. Or dosages and frequency may be in response to addiction symptoms, such as in a quantity and interval sufficient to curb the sensation of addiction withdrawal. In some instances, the device 12 may be used for entertainment purposes wherein dosages may be provided as desired.

In some embodiments, the delivery device 12 includes a filter 118, such as a flexible or rigid porous barrier, microperforated wall or mesh, along the volatile lumen 114 or the outlet opening 116 to assist in isolating the coffee substance 110. Such a filter 118 inhibits contact of the coffee substance 110 with the user's mouth or nose, and keeps the coffee substance 110 dry. This may be beneficial in ensuring that particles of coffee substance 110 do not enter the user's lungs during inhalation, thus avoiding any potential detrimental effects. In some embodiments, the delivery device 12 includes another filter 120 along the inlet lumen 106

The parts of the device 12 can be made of any combinations of polymers, silicone, wood, acrylic, paper, metal, cotton and other non-toxic materials. The device 12 is lightweight and easily handled, and its mounting parts can be recycled.

In some embodiments, the delivery device 12 is modular wherein portions of the device 12 may be removed and/or exchanged, such as to replace disposable parts. For example, the outlet opening 116 may include a mouthpiece to assist in delivery to the mouth. Such a mouthpiece may be interchangeable with a variety of different designs and/or be disposable. In addition, the chamber 108 and/or cartridge 112 may be attached to the mouthpiece, such as threaded in the mouthpiece, to allow insertion of the chamber 108 and/or cartridge 112 into the delivery device 12 upon attachment of the mouthpiece. Thus, the chamber 108 and/or cartridge 112 may be symmetric so as to be threadable in any direction. Likewise, the chamber 108 may be external to the device 112, attachable thereto when in use. Further, the delivery device 12 or portions thereof may be attached to other devices, such as for carrying convenience or to provide simultaneous delivery of coffee-derived volatiles 10 with the use of the other device.

In some embodiments, the delivery device 12 includes a one-way valve to release excess pressure built up within the device 12 due to the natural off gas process of roast and ground coffee. It is also believed that changes in external temperature and altitude can also cause the development of pressure internal to the device 12. The one-way valve is selected to release coffee off gas in excess of a predetermined amount however, remains sealed after such a release, thereby retaining an aromatically pleasing amount of off gassed product within the container.

Figure 7:
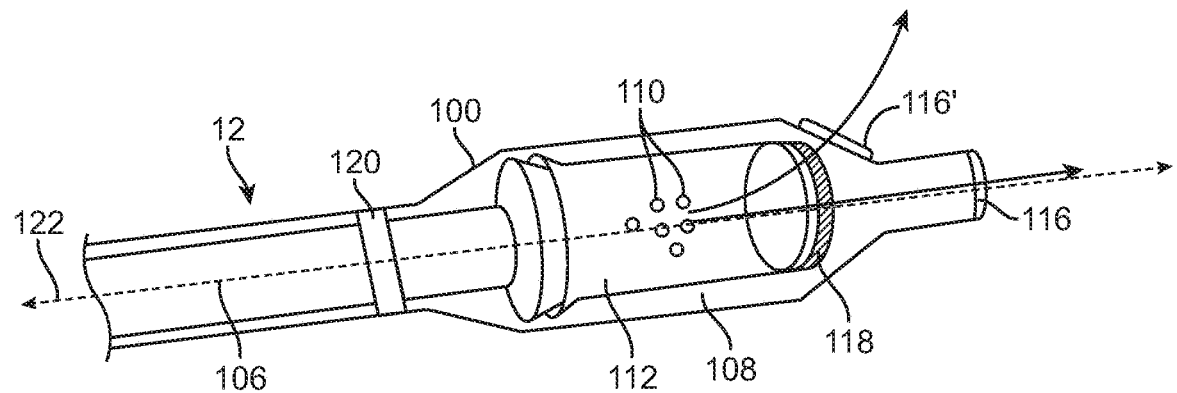
FIG. 7 illustrates an embodiment of a delivery device having a first outlet opening perpendicular to a longitudinal axis of the elongate shaft and a second outlet opening disposed at an angle to the longitudinal axis.
Figure 8:
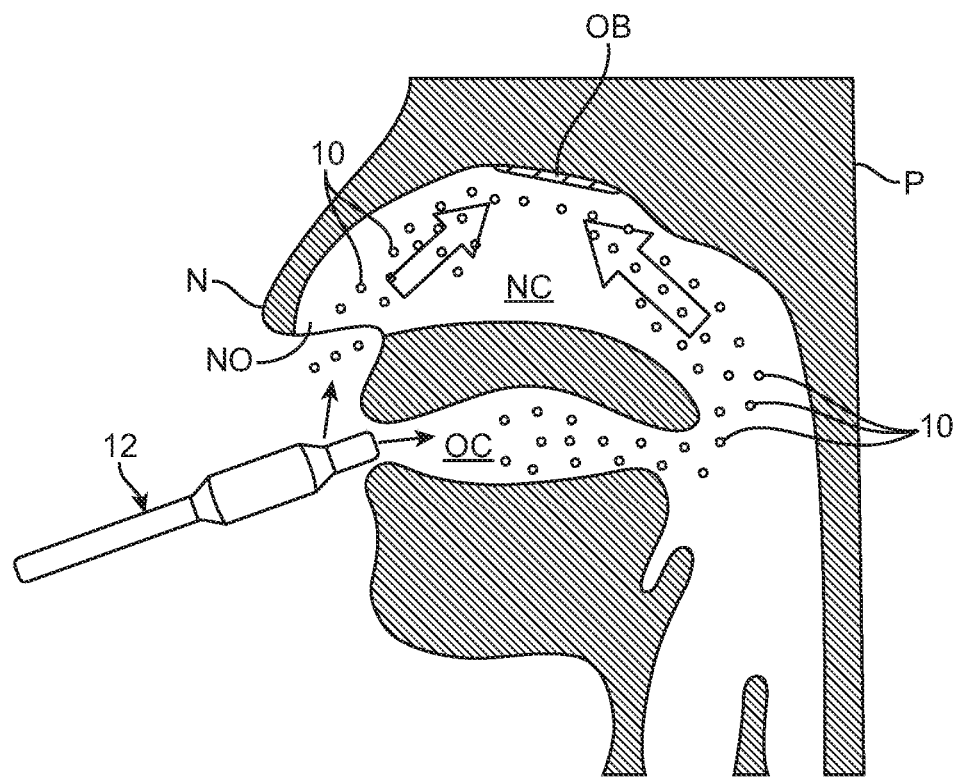
FIG. 8 illustrates the delivery device of FIG. 7 providing simultaneous orthonasal and retronasal delivery to a user.

It may be appreciated that the outlet opening 116 may be on any suitable surface of the elongate shaft 100. For example, the outlet opening 116 may be disposed along a side of the volatile lumen 114, such as to direct the volatiles 10 toward the nose N without tipping the device 12 upward. Similarly, the outlet opening may be disposed along a side of the chamber 108, such as to direct the volatiles 10 toward the nose N without tipping the device 12 upward. In such an embodiment, the filter 118 may also be disposed along the side of the chamber 108 proximal to the outlet opening 116. Likewise, more than one outlet opening 116 may be present. For example, FIG. 7 illustrates an embodiment of a delivery device 12 having a first outlet opening 116 perpendicular to a longitudinal axis 122 of the elongate shaft 100 and a second outlet opening 116' disposed at an angle to the longitudinal axis 122. In this embodiment, the second outlet opening 116' is positioned to direct volatiles 10 toward the nasal cavity NC while the first outlet opening 116 is positioned to direct volatiles 10 toward the oral cavity OC, as illustrated in FIG. 8. This allows simultaneous delivery to the olfactory bulb OB via the orthonasal and retronasal routes. Referring back to FIG. 7, in this embodiment, the filter 118 is positioned proximal to both outlet openings 116, 116' to assist in isolating the coffee substance 110.

Figure 9:
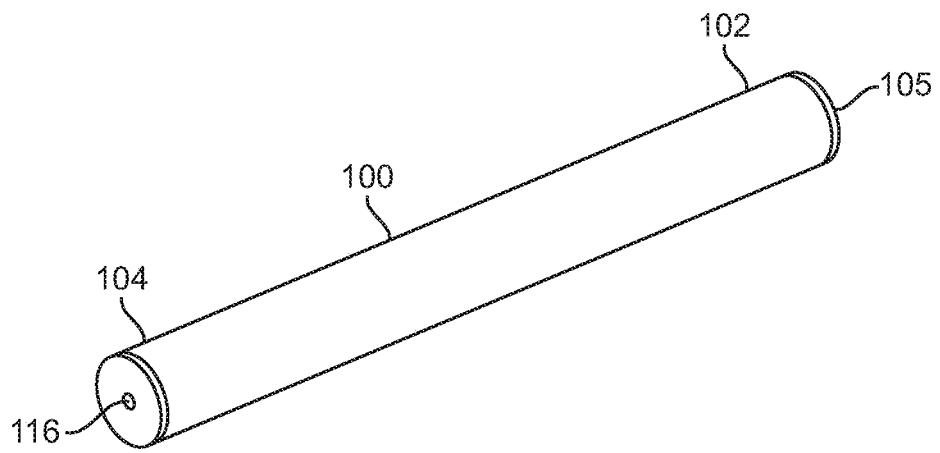
FIG. 9 illustrates an embodiment of a delivery device shaped and sized to resemble a cigarette.

As mentioned previously, the delivery device 12 may have a variety of shapes and sizes. In particular, the delivery device 12 may be designed to resemble accessories or devices associated with particular addictions. For example, as illustrated in FIG. 9, the delivery device 12 may be shaped and sized to resemble a cigarette. This may be useful in treating a smoking addiction. It is known that nicotine is the chemical in tobacco cigarettes that is addictive and keeps the user smoking even in the face of serious negative consequences. Nicotine is very addictive when delivered by inhaling tobacco smoke into the lungs, which quickly releases nicotine into the pulmonary circulation. The nicotine then enters the arterial circulation and moves quickly from the lungs to the brain, where it binds to nicotinic cholinergic receptors in the ventral tegmental area (VTA). After nicotine binds to the nicotinic receptor in the VTA, it results in release of neurotransmitters (dopamine) in the nucleus accumbens NA which is linked to reward, critical for the reinforcing effects (effects that promote self-administration) of nicotine. As previously described, controlled delivery of coffee-derived volatiles 10 is able to stimulate the brain reward system in the same or greater intensity as nicotine. Thus, the user may use a delivery device 12 containing coffee-derived volatiles 10 in place of a cigarette to treat the addiction to nicotine.

It is also known that smoking addiction involves various behavioral addictions in addition to the physiological addiction to nicotine. For example, smokers habituate to the feeling of holding a cigarette, utilizing their mouth, breathing in vapors, etc. In addition, behavioral associations with smoking may act as triggers—situations or feelings that activate a craving for tobacco, even if a physiological addiction to nicotine has been reduced or is absent. Example behaviors and situations may include certain times of the day (such as first thing in the morning, with morning coffee or during breaks at work), after a meal, when drinking alcohol, when in certain places or around certain friends, when seeing or smelling a cigarette, while talking on the phone, when feeling stressed, or when feeling depressed, to name a few. The delivery device 12 having the shape and size of a cigarette simulates the same cigarette-related habits and therefore can counter the behavioral addictions. Such as shape for the delivery device 12 may be even more effective due to habit similarity. Thus, the delivery device 12 allows the user to mimic the ritual of smoking without nicotine and toxic elements present even in e-cigarettes. The delivery device 12 also lacks the need for heating and has a low likelihood of addictive potential. At the same time, the low-profile design allows non-smokers to use it without relating it to smoking habits.

Figure 10:
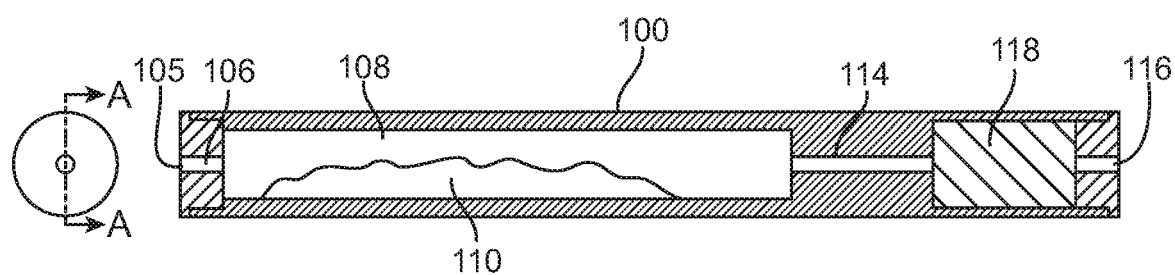
FIG. 10 illustrates a cross-sectional view of the delivery device of FIG. 9.

Referring to FIGS. 9-10, this embodiment of the delivery device 12 comprises an elongate shaft 100 having a first end 102 and a second end 104. In this embodiment, the first end 102 has an inlet opening 105 leading to an airway lumen 106. This allows air to flow into the delivery device 12. The airway lumen 106 leads to a chamber 108 which is configured to hold a coffee substance 110. The coffee substance 110 may comprise whole coffee beans, ground coffee, coffee oil with or without additives, single or mixed coffee molecules, each from natural or synthetic sources or any combination of these, to name a few. In some embodiments, the coffee substance 110 is further processed by the user to assist in release of coffee-derived volatiles 10 therefrom. For example, the user may grind whole coffee beans or bite or chew the ground coffee before it is inserted in the device. 12.

In this embodiment, the chamber 108 is connected with a volatile lumen 114 which extends to the second end 104 and an outlet opening 116. Thus, air is carried into the delivery device 12 through the inlet opening 105 and through the chamber 108 where it picks up coffee-derived volatiles 10 from the coffee substance 110. The coffee-derived volatiles 10 are then carried through the volatile lumen 114 and out the outlet opening 116. In this embodiment, the delivery device 12 includes a filter 118, such as a flexible or rigid porous barrier, micro-perforated wall or mesh, along the volatile lumen 114 proximal to the outlet opening 116 to assist in isolating the coffee substance 110. Such a filter 118 inhibits contact of the coffee substance 110 with the user's mouth, and keeps the coffee substance 110 dry. This may be beneficial in ensuring that particles of coffee substance 110 do not enter the user's lungs during inhalation, thus avoiding any potential detrimental effects.

In this embodiment, the coffee-derived volatiles 10 are typically delivered to the user retronasally (as in FIG. 1B) while the user mimics the act of smoking. Thus, air movement is typically assisted by sucking from the outlet opening 116 so as to draw air through the delivery device 12 and into the oral cavity OC. However, it may be appreciated that non-smokers may utilize this delivery device 12 design a variety of other manners, including orthonasal delivery.

In any case, airflow is typically actuated by the user to provide a discrete dose to the user. Each dose is sufficient to stimulate the brain reward system of the user. In particular, each dose is sufficient to stimulate the brain reward system, such as the ventral tegmental area VTA and/or nucleus accumbens NA, in an intensity equivalent to the use of a cigarette. Thus, the user is able to obtain the same or similar effect from a dose of coffee-derived volatiles 10 that the user would obtain from a cigarette, thereby allowing the user to eliminate smoking and its detrimental side effects.

Figure 11:
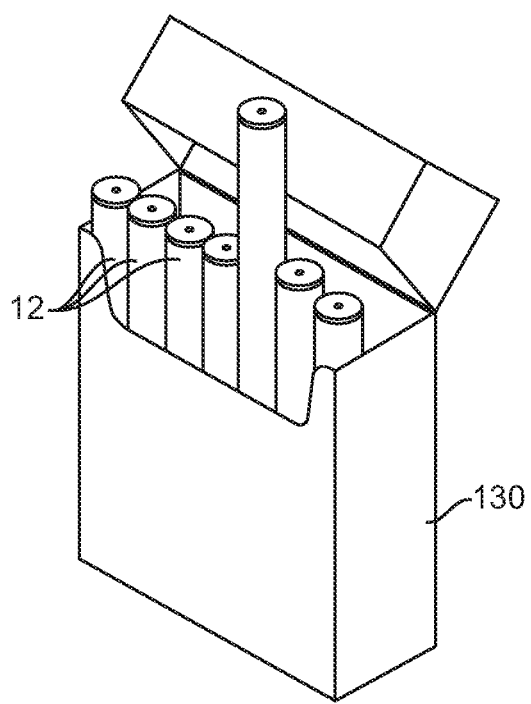
FIG. 11 illustrates a plurality of delivery devices packaged in a box so as to mimic a pack of cigarettes.

The delivery device 12 of FIGS. 9-10 is typically for single use. Each device 12 may be individually wrapped and provided with a desired quantity of coffee substance 110 pre-loaded in the chamber 108. Alternatively, a plurality of delivery devices 12 may be packaged in a box 130, as illustrated in FIG. 11, so as to mimic a pack of cigarettes. Such a display is familiar to a smoker and can readily replace a habit of cigarette carrying. It may be appreciated that each of the delivery devices 12 in the plurality of delivery devices 12 may be the same (i.e. have the same quantity of the same type of coffee substance 110 therein). It may also be appreciated that at least some of the delivery devices 12 in the plurality of delivery devices 12 may differ. In some embodiments, at least some of the delivery devices 12 have a different quantity of the same type of coffee substance 110 so as to provide a different dosage to the user. This may be helpful when the user is curtailing a smoking habit. Thus, individual delivery devices 12 may vary with lessening amounts of coffee substance 110 so as to provide a reduced dosage of coffee-derived volatiles 10 to the user with each device 12. It may be appreciated that in some embodiments, at least some of the delivery devices 12 have a different type of coffee substance 110 therein, such as providing a "variety pack".

Figure 12:
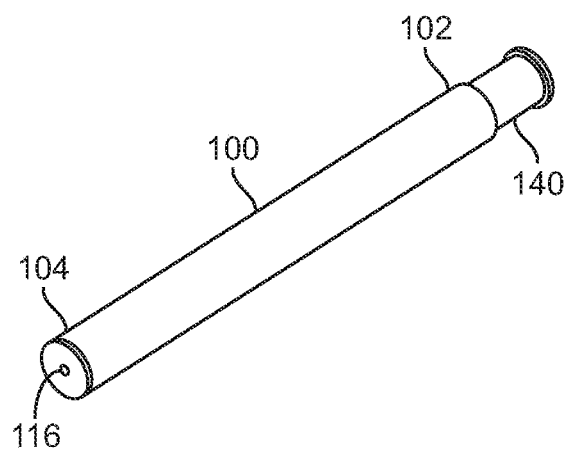
FIGS. 12-14 illustrate an embodiment of a delivery device having cartridge containing the coffee substance that is actuatable by movement of an end cap.
Figure 13:
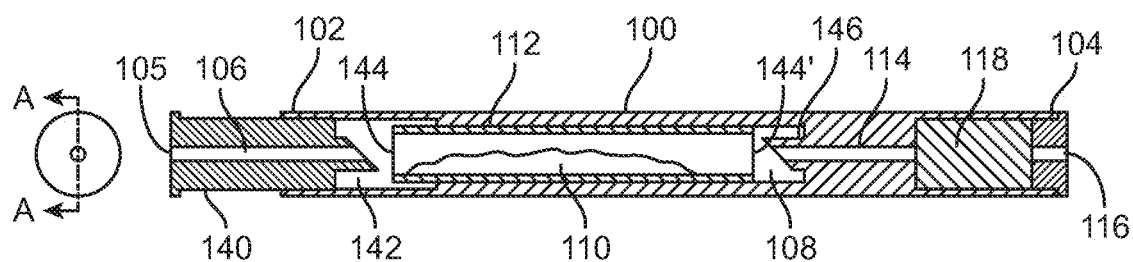
Figure 14:
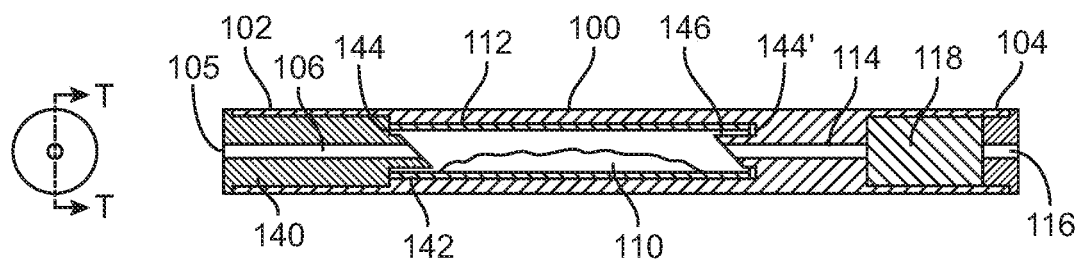

FIGS. 12-14 illustrate an embodiment of a delivery device 12 having an actuatable cartridge 112 containing the coffee substance 110. FIG. 12 provides a perspective view of this embodiment, wherein the delivery device 12 comprises an elongate shaft 100 having a first end 102 and a second end 104. The device 12 includes an end cap 140 which is insertable into the first end 102. As illustrated in FIG. 13, the end cap 140 includes an inlet opening 105 leading to an airway lumen 106. In addition, the end cap 140 includes a first protrusion 142 having an edge configured for puncturing a membrane, such as a pointed or beveled edge. In some embodiment, the end cap 140 is also removable so as to allow insertion of the cartridge 112 through the first end 102 to a location within the shaft 100. However, it may be appreciated that in some embodiments the end cap 140 is not removable wherein the cartridge 112 is preloaded into the shaft 100. In this embodiment, the cartridge 112 comprises a capsule having a puncturable surface 144, such as a membrane, facing the first protrusion 142 when inserted into the shaft 100.

In this embodiment, the chamber 108 has a second protrusion 146 directed therein, wherein the second protrusion 146 has an edge configured for puncturing a membrane, such as a pointed or beveled edge. Likewise, the cartridge 112 has an additional puncturable surface 144', such as a membrane, facing the second protrusion 146 when disposed in the shaft 100.

The cartridge 112 holds the coffee substance 110 which may comprise whole coffee beans, ground coffee, coffee oil with or without additives, single or mixed coffee molecules, each from natural or synthetic sources synthetic or any combination of these, to name a few. In this embodiment, the coffee substance 110 is sealed within the cartridge 112. In some embodiments, the cartridge 112 maintains an inert atmosphere such as by the inclusion of nitrogen and argon. Optionally, when the cartridge 112 is accessible to the user, the user may manipulate the cartridge 112 to further process the coffee substance 110, such as pressing the cartridge 112 between the fingers or chewing on the cartridge 112 to crush or activate the coffee substance 110 within. The user then inserts the cartridge 112 into the elongate shaft 100 and inserts the end cap 140 into the first end 102 of the elongate shaft 100. The user may maintain this arrangement until the point of use. When the user desires a dose of the coffee-derived volatiles 10, the user actuates the device 12 by pressing the end cap 140 into the first end 102, as illustrated in FIG. 14. Such pressing causes insertion of the first protrusion 142 into the puncturable surface 144 and the second protrusion 146 into the additional puncturable surface 144'. This activates the cartridge 112 allowing coffee-derived volatiles 10 to enter the volatile lumen 114 which extends to the second end 104 and an outlet opening 116. Thus, air is carried into the delivery device 12 through the inlet opening 105 and through the cartridge 112 where it picks up coffee-derived volatiles 10 from the coffee substance 110. The coffee-derived volatiles 10 are then carried through the volatile lumen 114 and out the outlet opening 116. In this embodiment, the delivery device 12 includes a filter 118, such as a flexible or rigid porous barrier, microperforated wall or mesh, along the volatile lumen 114 proximal to the outlet opening 116 to assist in isolating the coffee substance 110. This airflow is typically actuated by the user to provide a discrete dose to the user. Each dose is sufficient to stimulate the brain reward system of the user. After use, the device 12 may be disposed of or, when the cartridge is removable, the cartridge 112 may then be removed and replaced with a fresh cartridge 112.

It may be appreciated that in some embodiments, multiple cartridges 112 may be loaded into the delivery device 12 at the same time. For example, in some embodiments, two cartridges 112 may be loaded so that advancement of the end cap 140 into the first end 102 causes puncture of both cartridges 112. This provides a double dose of coffee-derived volatiles 10 to the user. It may be appreciated that the quantities and/or types of coffee substances 110 within the cartridges 102 may be varied to create personalized dosages when used together in various combinations. Likewise, the number of cartridges 112 may be varied to provide a personalized dose.

Figure 15A:
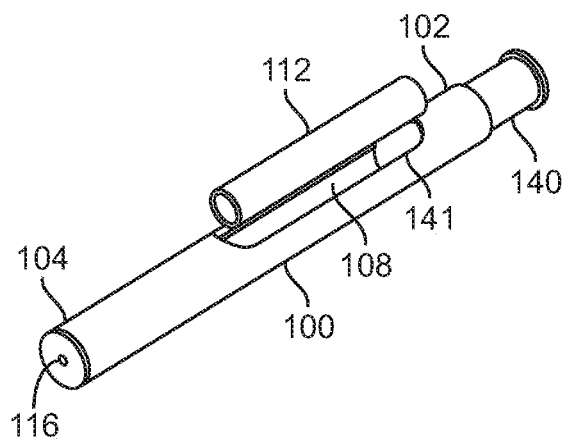
FIGS. 15A-15B illustrate an embodiment of a side-loading delivery device.
Figure 15B:
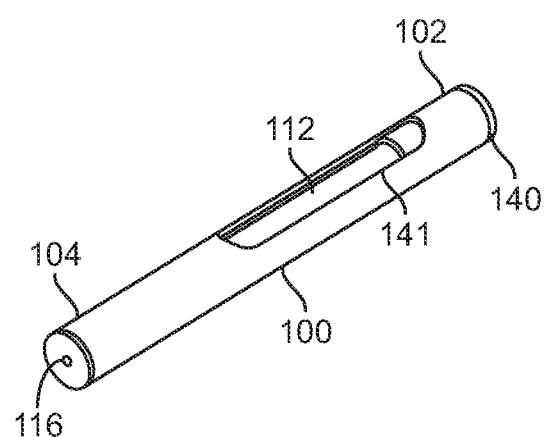
Figure 16A:
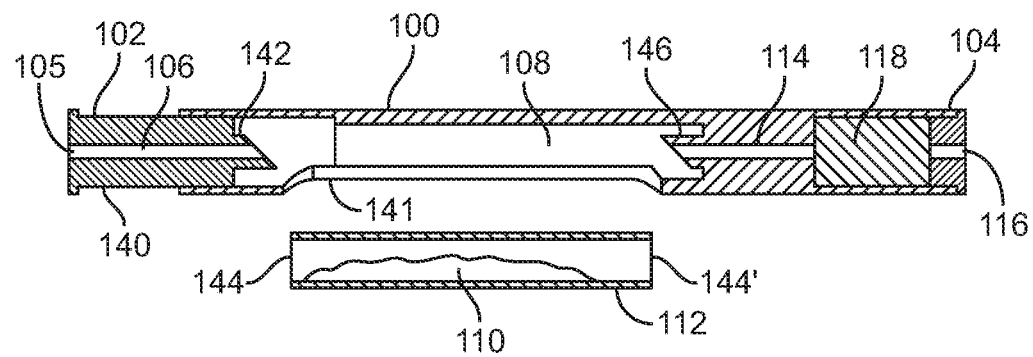
FIG. 16A provides a side cross-sectional view of the delivery device of FIG. 15A with the cartridge residing next to the opening.
Figure 16B:
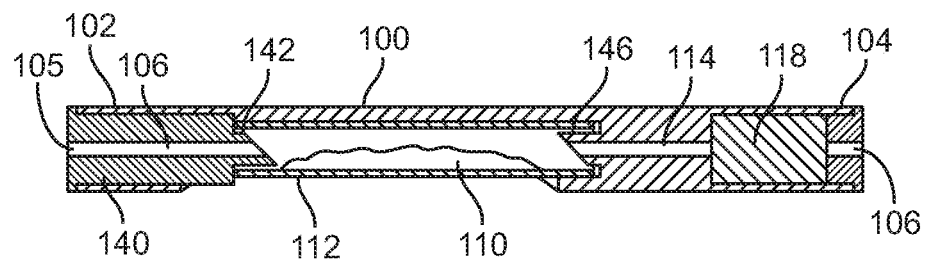
FIG. 16B provides a side cross-sectional view of the delivery device of FIG. 15B with the cartridge residing within the chamber.

It may also be appreciated the one or more cartridges 112 may be loaded into the one or more chambers 108 by a variety of methods and designs. FIGS. 15A-15B illustrate an embodiment of a side-loading delivery device 12. In this embodiment, the elongate shaft 100 includes an opening 141 along its circumferential wall. The opening is sized and shaped for insertion of a cartridge 112 therethrough into the chamber 108 within the shaft 100, as illustrated in FIG. 15A. FIG. 15B illustrates the cartridge 112 inserted through the opening 141 and residing within the chamber 108. FIG. 16A provides a side cross-sectional view of the delivery device 12 of FIG. 15A with the cartridge 112 residing next to the opening 141. Likewise, FIG. 16 B provides a side cross-sectional view of the delivery device 12 of FIG. 15B with the cartridge 112 residing within the chamber 108. FIG. 15B also illustrates the end cap 140 advanced therein so as to activate the cartridge 112 by puncturing with the first and second protrusions 142, 146. Activation of the cartridge 112 allows coffee-derived volatiles 10 to enter the volatile lumen 114 which extends to the second end 104 and an outlet opening 116. Thus, air is carried into the delivery device 12 through the inlet opening 105 and through the cartridge 112 where it picks up coffee-derived volatiles 10 from the coffee substance 110. The coffee-derived volatiles 10 are then carried through the volatile lumen 114 and out the outlet opening 116. After use, cartridge 112 is removed and replaced with a fresh cartridge 112.

Figure 17:
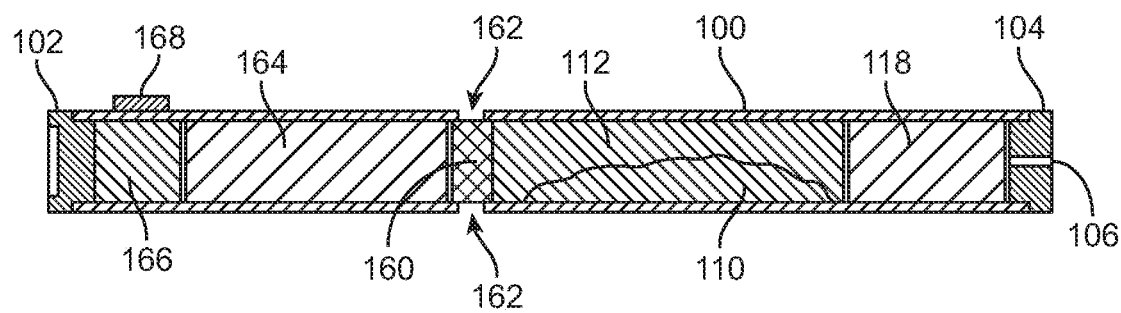
FIG. 17 illustrates an embodiment of a delivery device which includes an internal airflow accelerator.

FIG. 17 illustrates an embodiment of a delivery device 12 which includes an internal airflow accelerator 160 within elongate shaft 100 to propel the coffee-derived volatiles 10 out of the delivery device 12 and toward the user. In this embodiment, the mechanism 160 is disposed within the shaft 100 proximal to the cartridge 112. One or more side ports 162 along the shaft 100 are aligned with the mechanism 160 to allow air to be drawn through the one or more side ports 162 so as to propel the volatiles 10 of the coffee substance 110 from the cartridge 112, through the outlet opening 116 to the user. In this embodiment, the airflow accelerator 160 is powered by a battery 164 and is controlled by electronics 166. Thus, the user may actuate the device 12 by pressing an actuation button 168, or other actuation mechanism, which causes the internal airflow accelerator 160 to propel the volatiles 10. In some embodiments, the electronics 166 include a timer so as to maintain actuation of the airflow accelerator 160 for a predetermined time. In other embodiments, the electronics 166 communicate with one or more sensors which sense variables such as volatile concentration, wherein the electronics 166 maintain actuation of the airflow accelerator 160 according to the sensed information. In some embodiments, the electronics are pre-programmed and in other embodiments the electronics are programmable by the user.

It may be appreciated that the delivery device 12 may include a variety of features to enhance the user experience. For example, in some embodiments the delivery device 12 includes an alert feature or mechanism configured to deliver an alert to the user indicating that it is a preferred time to deliver a dose of coffee-derived volatiles 10. The alert may be auditory, such as a beep or alarm, or visual, such as a blinking or colored LED light, or both. Such alerts may vary to provide indications of different types of reminders. In some embodiments, the alert feature is configured to deliver an alert at a plurality of predetermined time periods. In some instances, the predetermined time periods correspond to a pattern of addiction. For example, if a smoker typically desires a cigarette every hour, the alert feature may be configured to deliver an alert every hour to assist the user in curbing a smoking addiction. Thus, the predetermined time periods may correspond to a pattern of an addiction. In some embodiments, the delivery device 12 is preprogrammed with the alert feature. In other embodiments, the alert feature is programmable. In some embodiments, programming the delivery device 12 causes the delivery device 12 to provide a series of alerts at predetermined times indicating a series of preferred times to actuate the delivery device 12 according to a schedule related to treatment of the addiction In some embodiments, the alert feature is programmable remotely with the use of a computer device, such as a smart phone, personal computer or other similar device, such as via cellular, WiFi or Bluetooth communications. This allows the alert feature to be set or modified remotely by the user or by a healthcare team associated with the user. In some embodiments, such programming of the alert feature is in response to direct input (such as keyed information or voice commands). Examples situations include commands from a healthcare provider or user input indicating events such as cravings, withdrawal symptoms or a panic moment (e.g., suicidal activity or about to consume illicit drug). In some embodiments, such programming of the alert feature is in response to analysis of collected data, such as usage data/compliance, health data, craving patterns, withdrawal patterns, or logging of stressful or eventful moments, along with intensity information (mild, moderate, severe). In some embodiments, the alert feature is automatically modified in response to data provided to the delivery device 12.

In some embodiments, the delivery device 12 itself collects data based on indicators or sensors within the device 12. For example, usage data may be collected by the delivery device 12. Such collection of usage data may allow a user and/or healthcare team associated with the user to analyze patterns of use, such as to ensure compliance, track changes, modify the dosing schedule, etc.

It may be appreciated that in some embodiments, data collected by the delivery device 12 and/or computer device in communication with the delivery device 12 may be transmitted to another user or external system, such as a physician or healthcare team associated with the user. Thus, others may be alerted to the behavior or feelings of the user. It may be appreciated that these aspects of the alert feature and other communication features described above may be provided by electronics 166 and/or other electronics. Likewise, in some embodiments, the delivery device 12 includes the capability of loading additional software features.

In some embodiments, the delivery device 12 includes features which simulate aspects of a particular addiction to be treated. For example, in some embodiments, the delivery device 12 includes the dispersion of a vapor to mimic the experience of smoking. Such a vapor is for visual effect. Likewise, in some embodiments, the delivery device 12 includes an illuminated end, such as provided by a red or amber colored LED light. Such a light is for visual effect to resemble the lit end of a cigarette. Each of these features are typically powered by an internal battery.

Figure 18:
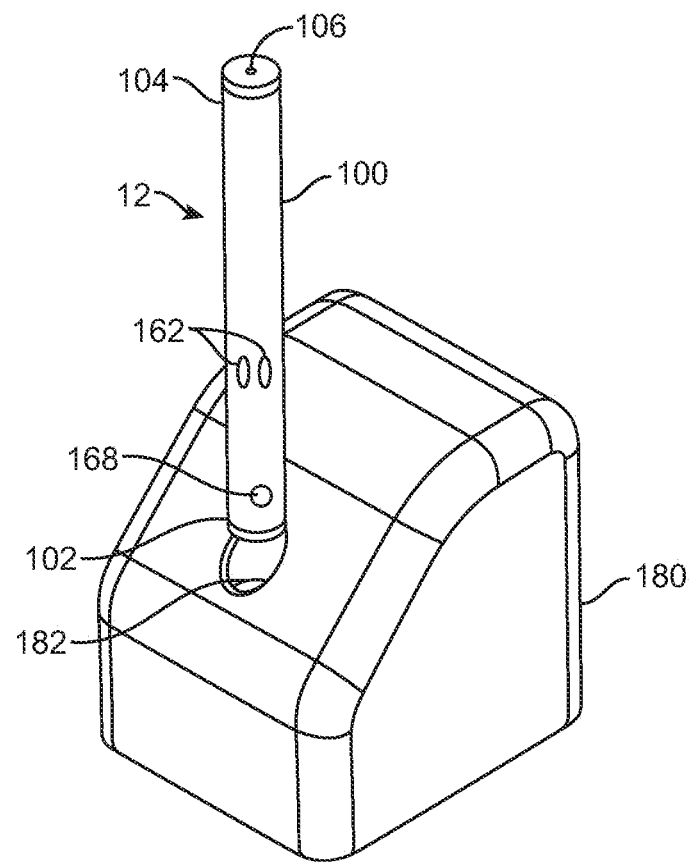
FIG. 18 illustrates an embodiment of a station for use with the delivery device.

FIG. 18 illustrates a station 180 for use with the delivery device 12. In some embodiments, the station 180 is used to recharge a battery, such as battery 164, within the delivery device 12. In such embodiments, the station 180 includes a charging port 182 for insertion of the first end 102 of the elongate shaft 100. The charging port 182 supplies energy to the battery 164, when the battery is rechargeable. In some embodiments, the station 180 is used to "recharge" the delivery device 12 with coffee substance 110. The station 180 may refill the chamber 108, such as by injection from a pressurized container within the station 180. Or, the station 180 may exchange or load a new cartridge 112 into the delivery device 12.

Figure 19:
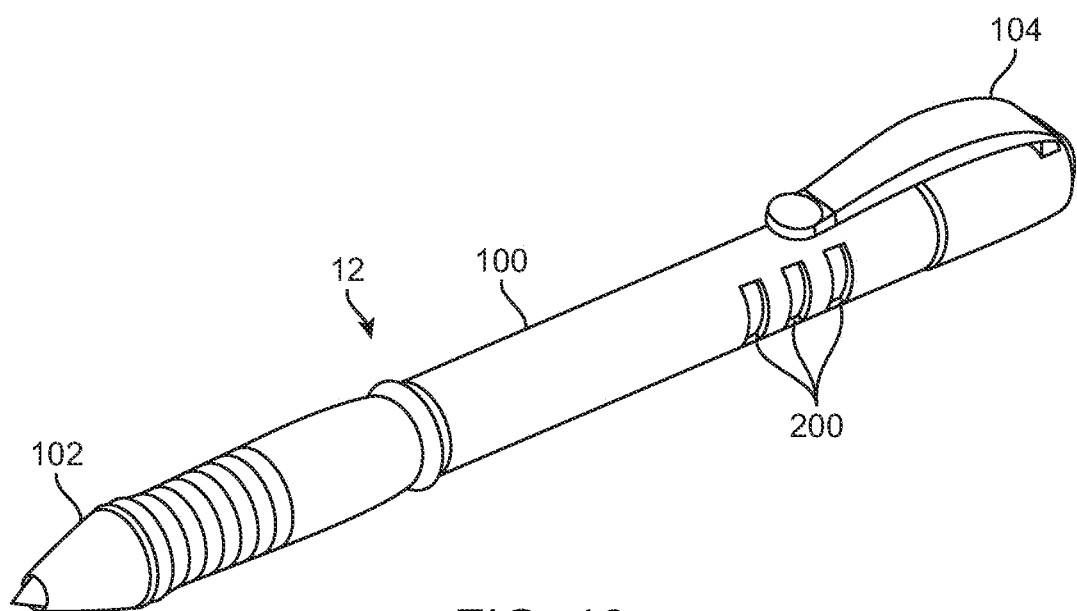
FIG. 19 illustrates an embodiment of a delivery device shaped and sized to resemble a pen or other writing implement.

As mentioned previously, the delivery device 12 may have a variety of shapes and sizes. In particular, the delivery device 12 may be designed to resemble everyday devices so as to be convenient and non-obvious to onlookers. For example, as illustrated in FIG. 19, the delivery device 12 may be shaped and sized to resemble a pen or other writing implement. In some embodiments, the delivery device 12 delivers coffee-derived volatiles 10 while also functioning as the device it resembles (e.g. the delivery device 12 may also function as a pen). In this embodiment, the delivery device 12 comprises an elongate shaft 100 having the shape of a pen. The elongate shaft 100 has a first end 102 for writing and a second end 104 which may be directed toward the user for coffee-derived volatile 10 inhalation.

FIG. 20 is a top view illustration of the delivery device 12 of FIG. 19. Likewise, FIG. 21 is a side view with a partial cross section of the delivery device 12 of FIG. 20. As shown in FIGS. 20-21, a cartridge 112 containing the coffee substance 110 is disposed within the elongate shaft 100. Again, the coffee substance 110 may comprise whole coffee beans, ground coffee, coffee oil with or without additives, single or mixed coffee molecules, each from natural or synthetic sources synthetic or any combination of these, to name a few. In this embodiment, a plurality of vent holes 200 are disposed along the elongate shaft 100 which allow both inlet flow of air into the cartridge 112 and outlet flow of coffee-derived volatiles 10 out of the cartridge 112 toward the user. In this embodiment, the vent holes 200 are closeable by rotation of a portion of the elongate shaft 100 which positions one or more covers 202 over the vent holes 200. FIG. 22A illustrates the device 12 in the "closed" position wherein the one or more covers 202 obstruct the vent holes 200. FIG. 22B is a close-up view of the vent holes 200 and covers 202 of FIG. 22A. The user keeps the device 12 in the closed position when not in use. This ensures that the volatiles 10 do not escape. When the user desires to receive a dose, the user actuates a mechanism to open the vent holes 200, such as by twisting a portion of the elongate shaft 100 to move the one or more covers 202 from obstructing the vent holes 200. FIG. 23A illustrates the device 12 in the "open" position wherein the one or more covers 202 are removed from obstructing the vent holes 200. FIG. 23B is a close-up view of the open vent holes 200 of FIG. 23A Thus, air is carried into the delivery device 12 through the vent holes 200 where it picks up coffee-derived volatiles 10 from the coffee substance 110. The coffee-derived volatiles 10 are then carried through to the user through the vent holes 200 as well. In this embodiment, the coffee-derived volatiles 10 are typically delivered to the user orthonasally (as in FIG. 1A) since it is common for people to hold the back ends of pens near their face and nose. However, it may be appreciated that users may also deliver the volatiles 10 retronasally as it is not uncommon for people to place the back ends of pens in their mouth.

In any case, airflow is typically actuated by the user to provide a discrete dose to the user. Each dose is sufficient to stimulate the brain reward system of the user. In particular, each dose is sufficient to significantly stimulate the brain reward system, such as the ventral tegmental area VTA and/or nucleus accumbens NA.

It may be appreciated that the delivery device 12 may be similarly shaped and configured to resemble and/or function as a wireless pen mouse, digital pen, smart pen or the like. These types of pens act as an input device which captures the handwriting or brush strokes of a user and converts handwritten analog information created using "pen and paper" into digital data, enabling the data to be utilized in various applications. This type of pen is usually used in conjunction with a digital notebook, although the data can also be used for different applications or simply as a graphic. The input device captures the handwriting data, that, once digitized, can be uploaded to a computer and displayed on its monitor. The data can then be interpreted by handwriting software (OCR) to allow the pen to act as a text entry interface and be used in different applications or just as graphics. In any case, the delivery device 12 would deliver coffee-derived volatiles 10 as described herein.

It may be appreciated that the delivery device 12 may be shaped and configured to be attached to or built into a variety of consumer devices, such as keychains, watches, hats, clothing, mobile phone cases, mobile phones, smart phones, Dictaphones, tablets, computers, music players, headphones, glasses cases, sunglass cases, water bottles, and clips to clip onto clothing, etc., to name a few.

Figure 24A:
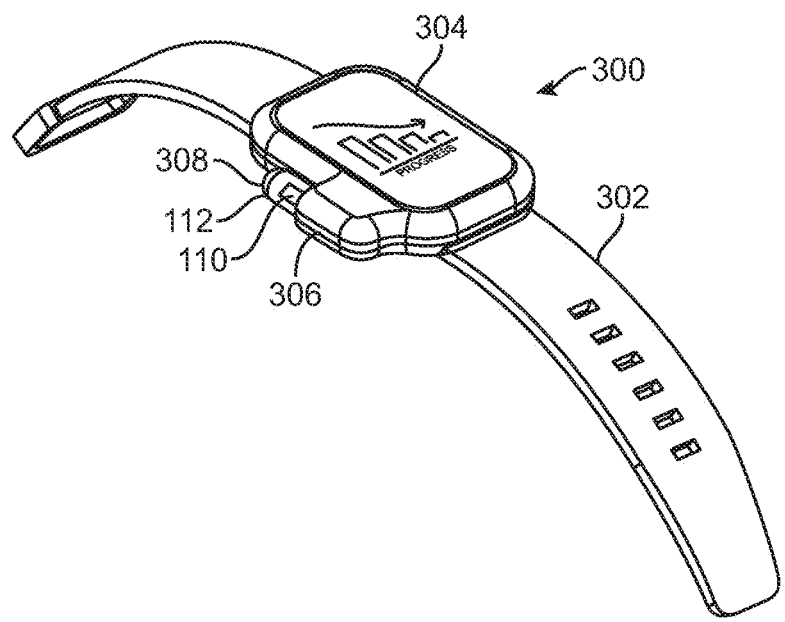
FIGS. 24A-24B illustrate an embodiment of a delivery device incorporated into a smart watch forming a volatile dispensing smart watch.
Figure 24B:
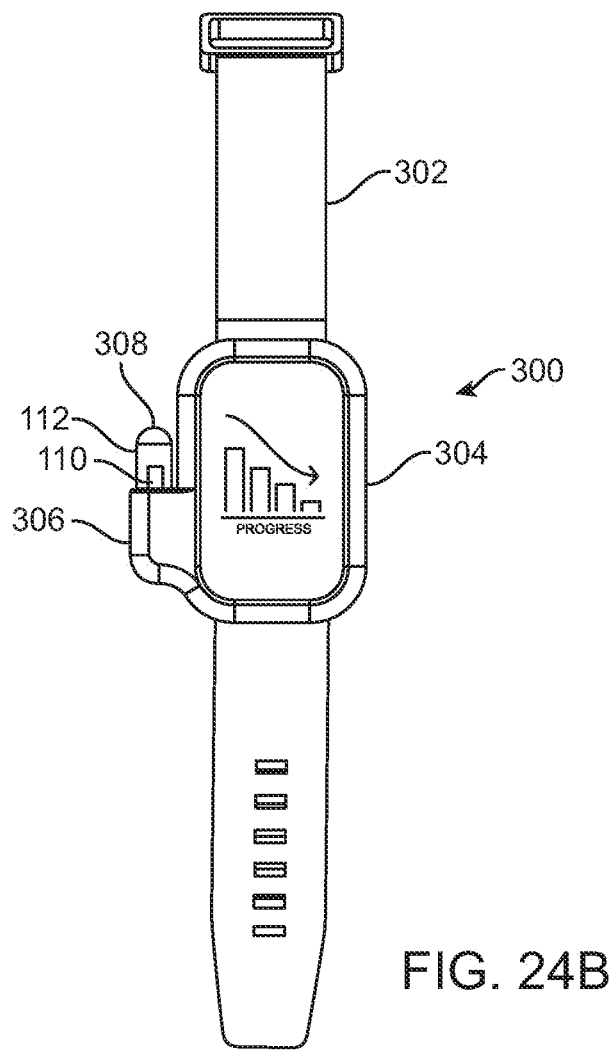

FIGS. 24A-24B illustrate an embodiment of a delivery device 12 incorporated into a smart watch forming a volatile dispensing smart watch 300. In this embodiment, the volatile dispensing smart watch 300 includes a wrist strap 302, and a watch body 304 having a "face" and electronics housed within. In this embodiment, the watch body 304 includes a receptacle 306 for receiving a cartridge 112 containing a coffee substance 110. The cartridge 112 includes at least one vent hole 308 which allows both inlet flow of air into the cartridge 112 and outlet flow of coffee-derived volatiles 10 out of the cartridge 112 toward the user. The cartridge 112 may be activated to release the coffee-derived volatiles 10 by a variety of mechanisms. In some embodiments, the insertion of the cartridge 112 into the receptacle 306 actuates the release of volatiles. Thus, the user places a cartridge 112 into the receptacle to receive a dose and removes the cartridge 112 when not in use. In other embodiments, the release of volatiles 10 is actuated by the electronics within the watch body 304. For example, the electronics may be programmable to release volatiles 10 at predetermined times or according to a predetermined schedule. Alternatively, the electronics may simply serve as a reminder system wherein the user actuates the release of volatiles 10 in response to the reminder system. It may be appreciated that the volatile dispensing smart watch 300 may provide a variety of features including: 1) tracking dosage information (including type, quantity, timing, etc), 2) tracking addiction treatment metrics, 3) tracking patient behavior/activity, 4) tracking vital signs, and 5) tracking user feedback, to name a few. Such tracking information may be displayed on the watch 300 and/or transmitted to various sources, such as social media. It may be appreciated that such features may also be provided when the delivery device 12 is incorporated into other types of smart devices, such as smart phones or computers. It may also be appreciated that the receptacle 306 for receiving the cartridge 112 may be built in or attachable to the smart watch 300 or other smart device. Likewise, the coffee substance may be carried by and attached to the smart watch 300 or other smart device by other mechanisms, such as with the use of microchips or aroma strips (paper, textile or other absorbent material containing coffee substance) which disperse volatiles 10.

In some embodiments, the delivery device 12 has the form or shape of an inhaler or nebulizer. FIGS. 25A-25B, 26 illustrate an embodiment of a volatile dispensing inhaler 400. FIG. 25A provides a perspective view and FIG. 26B provides a side view. FIG. 26 illustrates the internal mechanisms of the inhaler 400. In this embodiment, the volatile dispensing inhaler 400 includes a canister 402 which contains the coffee substance 110, such as coffee oil or coffee molecules. The canister 402 is positionable within a holder 404 and is removable for refilling with fresh coffee substance 110 or replacing with a fresh prefilled canister 402. The canister 402 is joinable with a metering valve 406 which meters the amount of coffee substance 110 drawn out of the canister 402. The metered amount is then advanced to a nozzle 408 which sprays the substance 110 out of an outlet opening 410 in a mist or aerosol. Once the coffee substance 110 has been released in this form, the coffee-derived volatiles 10 are easily airborne. The metering valve 406 allows for controlled delivery, providing a specific dose of volatiles 10 sufficient to stimulate the brain reward system according to the present invention. For retronasal delivery, the outlet opening 410 can be held near the mouth or inserted into the mouth. This allows the coffee-derived volatiles 10 to travel up to the olfactory bulb OB. For orthonasal delivery, the outlet opening 410 can be held near the nose which allows the coffee-derived volatiles 10 to travel through the nasal cavity to the olfactory bulb OB. It may be appreciated that the outlet opening 410 can also be held near the nose and mouth, at any distance, for simultaneous delivery via the orthonasal and retronasal routes.

It may be appreciated that the delivery device 12 having the form of a nebulizer would similarly deliver a mist or aerosol of liquid coffee substance or coffee molecules. Nebulizers use oxygen, compressed air or ultrasonic power to break up solutions and suspensions into small aerosol droplets that can be directly inhaled from a mouthpiece or outlet opening of the device. Example types of mechanical nebulizers include a soft mist inhaler and a human powered nebulizer. Example types of electrical nebulizers include a jet nebulizer (or atomizer), ultrasonic wave nebulizer, and vibrating mesh technology nebulizer. The device 12 would provide a specific dose of volatiles 10 sufficient to stimulate the brain reward system according to the present invention.

Figure 27:
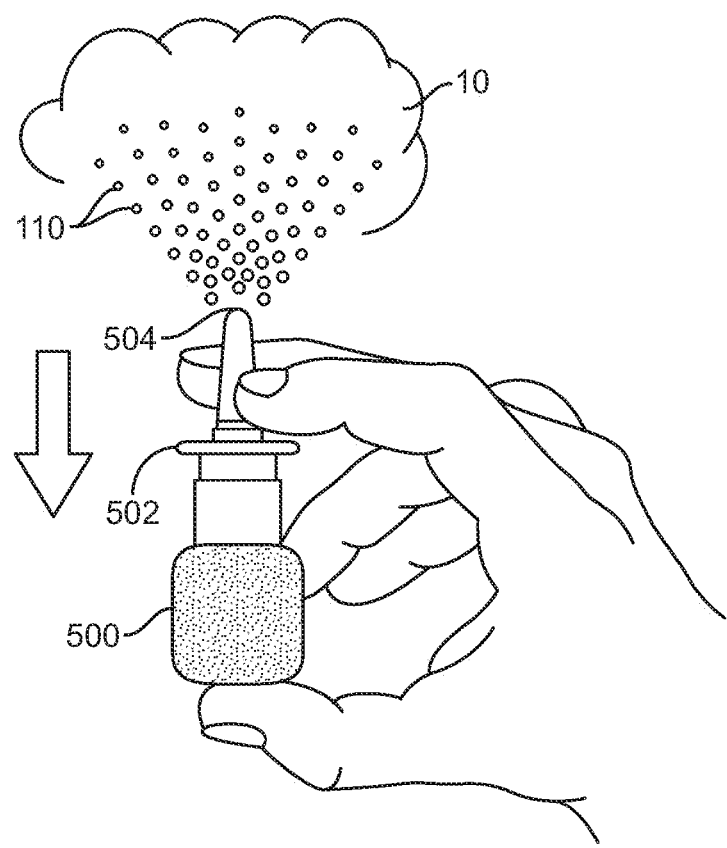
FIG. 27 illustrates an embodiment of a coffee-derived volatile dispensing spray container.

In some embodiments, the delivery device 12 has the form or shape of a spray container or an aerosol container. FIG. 27 illustrates an embodiment of a coffee-derived volatile dispensing spray container 500. The spray container 500 uses a positive displacement pump that acts directly on a liquid coffee substance. The pump draws the liquid coffee substance up a siphon tube from the bottom of the bottle and forces it through a nozzle. The nozzle may or may not be adjustable, so as to select between squirting a stream, aerosolizing a mist, or dispensing a spray. FIG. 27 illustrates a spray container 500 that functions similar to a nasal spray bottle. Here, the spray container 500 includes a flange 502 that is depressed with the finger to release a mist or spray of coffee substance 110 from an outlet opening 504. Once the coffee substance 110 has been released in this form, the coffee-derived volatiles 10 are easily airborne. The container 500 allows for controlled delivery, providing a specific dose of volatiles 10 sufficient to stimulate the brain reward system according to the present invention. For orthonasal delivery, the outlet opening 504 can be held near the nose N or passed through a nostril NO which allows the coffee-derived volatiles 10 to travel through the nasal cavity to the olfactory bulb OB. For retronasal delivery, the outlet opening 504 can be held near the mouth or inserted into the mouth. This allows the coffee-derived volatiles 10 to travel up to the olfactory bulb OB. It may be appreciated that the outlet opening 504 can also be held near the nose and mouth, at any distance, for simultaneous delivery via the orthonasal and retronasal routes.

Figure 28:
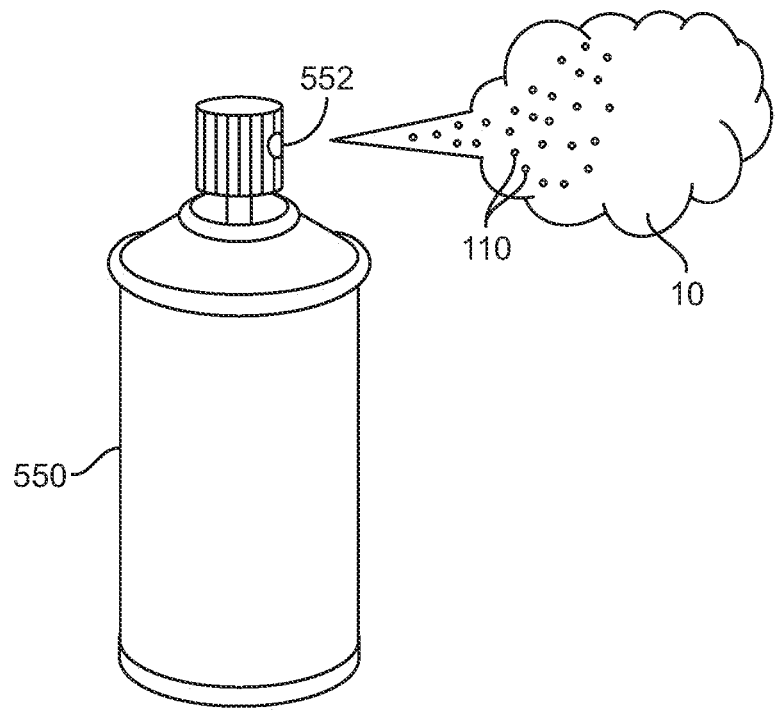
FIG. 28 illustrates an embodiment of a coffee-derived volatile aerosol container.

FIG. 28 illustrates an embodiment of a coffee-derived volatile aerosol container 550. While the spray container 500 has dispensing powered by the user's efforts, the aerosol container 550 is configured so that the user simply actuates a valve and the coffee substance 110 is dispensed under pressure. The coffee substance 110 emerges from an outlet opening 552. Once the coffee substance 110 has been released in this form, the coffee-derived volatiles 10 are easily airborne. The container 500 allows for controlled delivery, providing a specific dose of volatiles 10 sufficient to stimulate the brain reward system according to the present invention.

It may be appreciated that the inhaler 400, nebulizer, spray container 500 and aerosol container 550 are all configured for use in a manner which generates coffee-derived volatiles 10 for inhalation. It is the volatiles 10 which stimulate the olfactory bulb OB which in turn stimulates the reward system according to the present invention. It is desired to avoid inhalation of coffee substance particulate, such as coffee grounds, into the lungs. Thus, these types of delivery devices are preferably used with liquid coffee substances, such as coffee oil, or coffee molecules. Such liquid substances may be sprayed on the tongue, on the skin or on another portion of the anatomy which avoids inhalation of the liquid itself into the lungs. Likewise, such liquid substances may be sprayed into the air at a distance that the liquid itself is not inhaled into the lungs.

In some embodiments, the delivery device 12 has the form or shape of a nose plug or nostril cover. FIGS. 29A-29C illustrate an embodiment of a coffee-derived volatile dispensing nose plug 600. FIG. 29A provides a perspective view of the nose plug 600 and FIG. 29B provides a side cross-sectional view of the nose plug 600. In this embodiment, the nose plug 600 comprises at least one receptacle 602 for receiving a coffee substance 110. The coffee substance 110 may be pre-filled or inserted by the user in the receptacle 602 itself. Or, the coffee substance 110 may be contained in a cartridge, capsule, pouch, pod or other container to be inserted into the receptacle 602. Thus, the nose plug 600 may be single use or reusable depending on the receptacle design. The coffee substance 110 may be in a variety of forms including whole coffee beans, ground coffee, coffee oil with or without additives, single or mixed coffee molecules, each from natural or synthetic sources or any combination of these, to name a few. Substances that would not maintain position when the plug 600 is inverted would be disposed in a cartridge, capsule, pouch, pod or other container that would maintain position in the receptacle. Such a cartridge, capsule, pouch, pod or other container would be comprised of a porous material or would include at least one opening to allow release of the coffee-derived volatiles 10. Or, the receptacle 602 would be sealed, holding the coffee substance 110 therein. Likewise, in some embodiments, the coffee substance 110 is infused in a porous material within the receptacle 602 which maintains position. Each receptacle 602 includes an outlet opening 604 for dispersal of coffee-derived volatiles 10 from the coffee substance 110. In some embodiments, the nose plug 600 includes a bridge 606 which connects two receptacles 602 and maintains a predetermined distance between them and alignment in relation to each other. FIG. 29C illustrates the embodiment of FIGS. 29A-29B in use. In this embodiment, two receptacles 602, 602' are present, each inserted into a nostril NO of the nose N while the bridge 606 remains exterior to the nose N. Thus, the bridge 606 is sized and configured to hold the receptacles 602, 602' at a distance equivalent to the natural spacing of nostrils. In some embodiments, the bridge 606 is malleable to adjust the distance to adapt to different sized noses. Likewise, in some embodiments, the bridge 606 is malleable to adjust the alignment between the receptacles 602, 602' to adjust for natural anatomical differences. Once the receptacles 602, 602' are positioned within the nostrils NO, the coffee-derived volatiles 10 dispense into the nasal cavity NC and stimulate the olfactory bulb OB. In some embodiments, the user inhales through the receptacle, drawing the volatiles 10 into the nasal cavity NC. Doss are controlled by the type and quantity of coffee substance 110 contained therein along with the wearing schedule. Thus, controlled delivery is achieved, providing a specific dose of volatiles 10 sufficient to stimulate the brain reward system according to the present invention.

It may be appreciated that in some embodiments, the receptacles 604, 604' are not connected by a bridge 606 or are used individually. Likewise, it may be appreciated, the in some embodiments only one receptacle 604 includes a coffee substance 110. Further, it may be appreciated, the in some embodiments, the coffee substance 110 is packaged in a capsule or similar container and inserted into the nostril NO directly. In such embodiments, the capsule or similar container would be comprised of a porous material or would include at least one opening to allow release of the coffee-derived volatiles 10. Such positioning would allow discreet usage without visibility to onlookers.

Figure 30A:
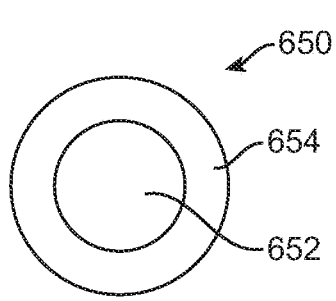
FIGS. 30A-30C illustrate an embodiment of a coffee-derived volatile dispensing nostril cover.
Figure 30B:
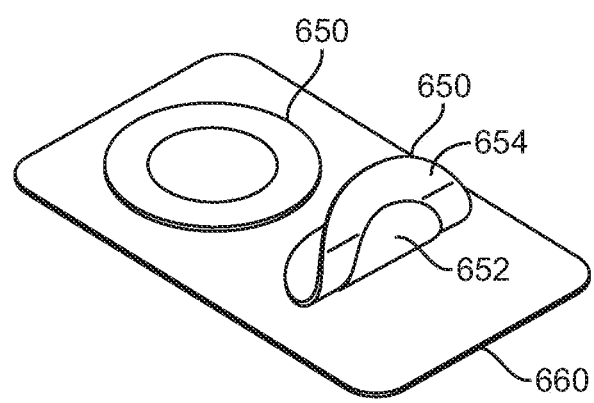
Figure 30C:
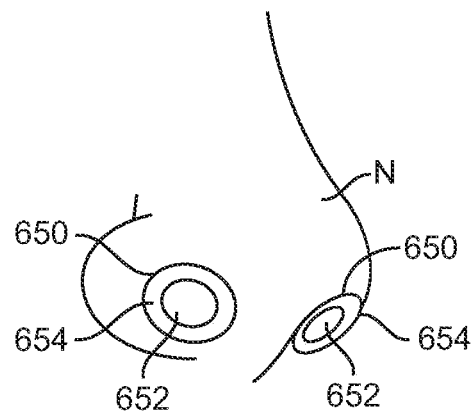

FIGS. 30A-30C illustrate an embodiment of a coffee-derived volatile dispensing nostril cover 650. FIG. 30A provides a perspective view of the nostril cover 650. In this embodiment, the nostril cover 650 comprises a mesh material 652 and an adhesive backing 654. The mesh material 652 is infused with a coffee substance 110. The mesh material 652 is sized and shaped to cover a nostril NO of a nose N. Thus, it is typically circular or oval. The adhesive backing 654 is sized and shaped to adhere to the exterior skin around the nostril NO. FIG. 30B illustrates an embodiment of packaging for the nostril covers 650. In this embodiment, the packaging comprises a sheet 660 to which the covers 650 are adhered when not in use. The adhesive backing 654 includes adhesive around the mesh material 652 so as to adhere the cover 650 to the sheet 660. In this embodiment, the adhesive backing 654 does not include adhesive on its side opposite the mesh 652. The sheet 660 and adhered covers 650 are stored in an airtight package when not is use so as to ensure coffee-derived volatiles 10 are not released when not in use.

FIG. 30C illustrates the embodiment of FIG. 30A in use. Here, each nostril cover 650 is shown adhered to the nose N of a user so that each mesh material 652 aligns with each nostril NO. The adhesive backing 654 adheres to the skin around the nostril NO. Thus, as the user inhales through the nostrils NO, and therefore though the mesh material 652 infused with coffee substance 110, coffee-derived volatiles 10 are drawn into the nasal cavity NO and stimulate the olfactory bulb OB. Doss are controlled by the type and quantity of coffee substance 110 contained therein along with the wearing schedule. Thus, controlled delivery is achieved, providing a specific dose of volatiles 10 sufficient to stimulate the brain reward system according to the present invention.

Addictions

As mentioned previously, the devices, systems and methods described herein are provided for delivering coffee-derived volatiles to a user, particularly for the treatment of addiction. The coffee volatiles are selected and delivered by devices and systems which allow for concentrated delivery to the olfactory system of the user in a controlled manner. Olfaction of such coffee volatiles in this prescribed fashion stimulates the reward system of the brain such that a specific desired outcome is achieved. In some embodiments, the desired outcome is a reduction in addiction symptoms or curbing of a sensation of addiction withdrawal. This is possible, at least in part, due to the unexpected potency of coffee volatiles in stimulating the reward system when delivered in this manner; such potency is comparable to stimulant drugs such as cocaine, opioids and nicotine. Addictive drugs produce a high by overstimulating the brain's reward system (much more than natural rewards do—up to 10 times more) by directly raising the levels of dopamine. Drugs of abuse affect the ventral tegmental area VTA—nucleus accumbens NA pathway with a power and persistence not seen in response to natural rewards.

It may be appreciated that any of the above described delivery devices 12 may be used to treat a particular addiction. For example, a patient with a nicotine addiction may prefer a delivery device resembling a cigarette, however such a patient may alternatively prefer a more discrete delivery device, such as a nasal cover. It may also be appreciated that any of the above described delivery devices may be specialized to provide a particular dose. Such doses may be chosen to correspond to a particular type of addiction (such as to heroin, cocaine, alcohol, opioids, nicotine, methamphetamine, caffeine, etc.) and/or a particular level of addiction. Likewise, delivery devices 12 (optionally providing differing doses) may be prescribed to a patient along with a dosage schedule so as to effectively treat an addiction over time. Similarly, delivery devices 12 may be pre-packaged according to a desired treatment plan, such as a "smoking cessation treatment plan".

It may be appreciated that the delivery devices may alternatively be used as needed, rather than according to a predetermined plan. In such instances, the user typically actuates the delivery device upon sensation of addiction withdrawal. Examples of withdrawal symptoms include emotional instability, anxiety, depression, irritability, restlessness, insomnia, sweating, hot flashes, lack of appetite, increased appetite, increased sensitivity to pain, and flu-like symptoms such as weakness, body aches and headaches. Actuating the delivery device, delivers the coffee-derived volatile to the patient so as to cause olfactory stimulation of the brain reward system in an intensity sufficient to curb the sensation of addiction withdrawal.

It may be appreciated that the delivery devices 12 may be used to treat behavioral addictions as well as addictions to substances. Behavioral addiction is a form of addiction that involves a compulsion to engage in a rewarding non-drug-related behavior—sometimes called a natural reward—despite negative consequences to the person's physical, mental, social or financial well-being. Examples include addictions to sex, gambling, shopping, eating, exercising, video games, television, and pornography, to name a few. Conventional treatment options for behavioral addictions include psychotherapy, such as cognitive behavioral therapy (CBT). Currently, there are no medications approved for treatment of behavioral addictions in general. However, the delivery of coffee-derived volatiles according to the present invention may be used to treat behavioral addictions. In some embodiments, the user actuates the delivery device upon a sensation of urging, wanting or desire to engage in the addictive behavior. Actuating the delivery device, delivers the coffee-derived volatile to the user so as to cause olfactory stimulation of the brain reward system in an intensity sufficient to curb the sensation. Consequently, the brain reward system is stimulated without engaging in the behavior and the addiction is able to wane or disappear.

Entertainment

It may be appreciated that although the delivery devices of the present invention are capable of stimulating the brain reward system at an intensity comparable to stimulant drugs, and therefore are able to treat addiction to such drugs, the delivery devices may also be used simply for entertainment purposes. Thus, the delivery devices may be used for inducing neural and/or psychological states associated with hedonic (pleasurable or rewarding) experiences for recreational purposes.

Other Substances

It may be appreciated that although the delivery devices of the present invention are described to be used with coffee substances to deliver coffee-derived volatiles, the delivery devices may be filled with other substances for delivery of other volatiles for different effects. A neurological effect, if any, would depend on the substances used and volatiles produced. Likewise, it may be appreciated that additional substances and additives may be included in the coffee substance to provide additional effects. The type and intensity of such effects would depend on the substances added and volatiles produced.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for delivering coffee-derived volatiles to a user comprising:
    a housing body;
    a quantity of coffee substance disposed within the housing body such that coffee-derived volatiles are collectable within the housing body from the coffee substance without a use of heat wherein the quantity of coffee substance is provided in a removable cartridge, the cartridge having at least one puncturable wall; and
    an actuatable mechanism for allowing user actuated delivery of a discrete dose of the coffee-derived volatiles from the housing body to the user's olfactory system, the actuable mechanism comprising a protrusion configured to puncture the at least one puncturable wall upon actuation so as to allow the delivery of the coffee-derived volatiles, wherein the delivered dose and composition of the coffee-derived volatiles allow for olfactory stimulation of a ventral tegmental area or nucleus accumbens of a brain reward system of the user in an intensity equivalent to that produced by use of an addictive drug.

2. A device as in claim 1, wherein the intensity is equivalent to that produced by use of heroin, cocaine, alcohol, opioids, nicotine, amphetamine, methamphetamine, caffeine.

3. A device as in claim 1, wherein the intensity allows for curbing of a withdrawal sensation of an addiction.

4. A device as in claim 1, wherein the coffee substance comprises ground coffee and the quantity of ground coffee is 10 grams.

5. A device as in claim 1, wherein the coffee substance comprises whole coffee beans, ground coffee, coffee oil, single or mixed coffee molecules, or any combination of these.

6. A device as in claim 1, wherein the quantity of coffee substance is in range from 9 to 11 grams.

7. A device as in claim 6, wherein the quantity of coffee substance is in a range from about 9.5 to 10.5 grams.

8. A device as in claim 1, wherein the removable cartridge is sufficiently flexible to allow the user to reversibly deform the cartridge so as to further process the coffee substance therein.

9. A device as in claim 1, wherein the removable cartridge is pre-filled and sealed.

10. A device as in claim 1, wherein the removable cartridge is refillable by the user.

11. A device as in claim 1, wherein the removable cartridge comprises a plurality of removable cartridges, wherein the plurality of removable cartridges is positionable within the housing body.

12. A device as in claim 1, wherein the actuatable mechanism comprises an internal airflow accelerator configured to propel the volatiles.

13. A device as in claim 1, wherein the actuatable mechanism comprises a depressible button, wherein depression of the button actuates the actuatable mechanism.

14. A device as in claim 1, further comprising at least one outlet opening disposed along the housing body and configured for passage of the coffee-derived volatiles from the housing body.

15. A device as in claim 14, wherein the actuatable mechanism comprises at least one cover that is moveable from a first position which blocks the at least one outlet opening from passage of the coffee-derived volatiles to a second position which exposes the at least one outlet opening for passage of the coffee-derived volatiles.

16. A device as in claim 14, wherein the at least one outlet opening comprises a plurality of outlet openings arranged to provide simultaneous orthonasal and retronasal delivery of the coffee-derived volatiles.

17. A device as in claim 1, wherein the housing body has a form of an elongate shaft.

18. A device as in claim 17, wherein the actuatable mechanism comprises an end cap joinable with an end of the elongate shaft, wherein joining of the end cap with the end of the elongate shaft actuates the actuatable on mechanism.

19. A device as in claim 18, wherein the end cap includes the protrusion configured to puncture the at least one puncturable wall upon joining of the end cap with the end of the elongate shaft.

20. A device as in claim 17, wherein the elongate shaft resembles a cigarette, e-cigarette or cigar.

21. A device as in claim 17, wherein the elongate shaft resembles a pen or writing implement.

22. A device as in claim 17, wherein the elongate shaft is configured to be insertable into a receptacle on a keychain, watch, hat, article of clothing, mobile phone case, mobile phone, smart phone, Dictaphone, tablet, computer, music player, headphone, glasses case, sunglass case, water bottle, or clip.

23. A device as in claim 1, wherein the housing body has a form of a nose plug or nostril cover.

24. A device as in claim 1, further comprising a filter configured to inhibit delivery of the coffee substance from the housing body.

25. A device for delivering coffee-derived volatiles to a user comprising:
    a housing body;
    a quantity of coffee substance disposed within the housing body such that coffee-derived volatiles are collectable within the housing body from the coffee substance without the use of heat;
    an actuatable mechanism for allowing user actuated delivery of a discrete dose of the coffee-derived volatiles from the housing body to the user's olfactory system, wherein the delivered dose and composition of the coffee-derived volatiles allow for olfactory stimulation of a ventral tegmental area or nucleus accumbens of a brain reward system of the user in an intensity equivalent to an addictive drug; and an alert mechanism configured to deliver an alert at a plurality of predetermined time periods, wherein the time periods correspond to a pattern of an addiction.

26. A method of treating an addiction of a patient comprising;
providing a delivery device configured to deliver a discrete dose of coffee-derived volatiles upon actuation, wherein the coffee-derived volatiles are generated by the delivery device without a use of heat and the delivery device includes at least one outlet opening for passage of the volatiles therethrough, the dose and composition of the coffee-derived volatiles allowing for a statistically significant amount of stimulation of a ventral tegmental area or nucleus accumbens of a reward system of the patient's brain;
inserting a pre-filled cartridge containing coffee substance into the delivery device;
positioning the delivery device in relation to the patient so that the at least one outlet opening of the device is within a distance which allows olfactory stimulation of the patient by the coffee-derived volatiles upon their delivery; and
actuating the delivery device upon a sensation of addiction withdrawal, wherein actuating delivers a phasic dose of coffee-derived volatiles through the at least one outlet opening to the patient which causes olfactory stimulation of the brain reward system of the patient allowing for curbing a sensation of addiction withdrawal.

27. The method of claim 26, wherein the addiction comprises nicotine addiction, opioid addiction, cocaine addiction, methamphetamine addiction, heroin addiction or alcohol addiction.

28. The method of claim 27, wherein the sensation of addiction withdrawal comprises irritability, restlessness, anxiety, depression, sleeplessness or cravings.

29. The method of claim 26, wherein the olfactory stimulation comprises orthonasal stimulation and positioning the delivery device comprises holding the at least one outlet opening within 3 cm of a nostril of the patient.

30. The method of claim 26, wherein the olfactory stimulation comprises retronasal stimulation and positioning the delivery device comprises positioning the at least one outlet opening within an oral cavity of the patient.

31. The method of claim 26, wherein a quantity of coffee substance in the pre-filled cartridge is in a range from about 9 to 11 grams.

32. The method of claim 31, wherein the quantity of coffee substance in the pre-filled cartridge is in a range from about 9.5 to 10.5 grams.

33. The method of claim 26, wherein actuating the delivery device comprises puncturing the cartridge so as to allow escape of the coffee-derived volatiles.

34. The method of claim 26, further comprising reversibly deforming the cartridge so as to further process the coffee substance therein.

35. The method of claim 26, wherein actuating the delivery device comprises opening a cover over at least one of the at least one outlet openings.

36. The method of claim 26, wherein actuating the delivery device is undertaken in accordance with a predetermined schedule.

37. A method of treating an addiction of a patient comprising:
providing a delivery device configured to deliver a discrete dose of coffee-derived volatiles upon actuation, wherein the coffee-derived volatiles are generated by the delivery device without the use of heat and the delivery device includes at least one outlet opening for passage of the volatiles therethrough, the dose and composition of the coffee-derived volatiles allowing for a statistically significant, amount of stimulation of a ventral tegmental area or nucleus accumbens of a reward system of the patient's brain;
positioning the delivery device in relation to the patient so that the at least one outlet opening of the device is within a distance which allows olfactory stimulation of the patient by the coffee-derived volatiles upon their delivery;
actuating the delivery device upon a sensation of addiction withdrawal, wherein actuating delivers a phasic dose of coffee-derived volatiles through the at least one outlet opening to the patient which causes olfactory stimulation of the brain reward system allowing for curbing a sensation of addiction withdrawal; and
programming the delivery device to provide an alert at a predetermined time indicating a preferred time to actuate the delivery device.

38. The method of claim 37, wherein programming the delivery device comprises programming the delivery device to provide a series of alerts at predetermined times indicating a series of preferred times to actuate the delivery device according to a schedule related to treatment of the addiction.

39. A method of treating an addiction of a patient, comprising:
providing a delivery device configured to deliver a discrete dose of coffee-derived volatiles upon actuation, wherein the coffee-derived volatiles are generated by the delivery device without the use of heat and the delivery device includes at least one outlet opening for passage of the volatiles therethrough, the dose and composition of the coffee-derived volatiles allowing for a statistically significant, amount of stimulation of a ventral tegmental area or nucleus accumbens of a reward system of the patient's brain;
positioning the delivery device in relation to the patient so that the at least one outlet opening of the device is within a distance which allows olfactory stimulation of the patient by the coffee-derived volatiles upon their delivery;
actuating the delivery device upon a sensation of addiction withdrawal, wherein actuating delivers a phasic dose of the coffee-derived volatiles through the at least one outlet opening to the patient which causes olfactory stimulation of the brain reward system of the patient allowing for curbing a sensation of addiction withdrawal; and
attaching the delivery device to a keychain, watch, hat, article of clothing, mobile phone case, mobile phone, smart phone, Dictaphone, tablet, computer, music player, headphone, glasses case, sunglass case, water bottle, or clip.

40. A smart watch for delivery of coffee-derived volatiles to a user, the smart watch comprising:
a watch body and a wrist strap attached to the watch body, the watch body having a face and electronics housed within the watch body;
a receptacle coupled to the watch body; the receptacle for receiving a cartridge containing a coffee substance, the coffee substance releasing coffee derived volatiles (CDV) from the cartridge when exposed to airflow; and a mechanism for release and delivery of a discrete dose of CDV from the cartridge to the user's olfactory system, wherein the delivered dose and composition of the CDV allow for olfactory stimulation of a ventral tegmental area or nucleus accumbens of a brain reward system.

41. The smart watch as in claim 40, wherein insertion of the cartridge into the receptacle actuates release of the CDV.

42. The smart watch as in claim 40, wherein the electronics control release of the CDV from the cartridge.

43. The smart watch as in claim 42, wherein the electronics are programmable to release the CDV at predetermined times.

44. The smart watch as in claim 40, wherein the electronics track user information.

45. The smart watch as in claim 44, wherein the user information is at least one of dosage information, an addiction treatment metric, user behavior, user activity, user vital signs or user feedback.

46. The smart watch as in claim 44, wherein the electronics display the tracked user information on the smart watch.

* * * * *